United States Patent [19]
Hashimoto et al.

[11] Patent Number: 5,649,955
[45] Date of Patent: Jul. 22, 1997

[54] SURGICAL INSTRUMENT

[75] Inventors: Daijo Hashimoto, Tokyo; Takatomo Hisamatsu, Kanagawa; Itaru Okubo, Kanagawa; Masahiro Nudeshima, Kanagawa, all of Japan

[73] Assignees: Terumo Kabushiki Kaisha; Daijo Hashimoto, both of Tokyo, Japan

[21] Appl. No.: 405,786

[22] Filed: Mar. 17, 1995

[30] Foreign Application Priority Data

| Mar. 17, 1994 | [JP] | Japan | 6-73968 |
| Mar. 17, 1994 | [JP] | Japan | 6-73969 |
| Mar. 17, 1994 | [JP] | Japan | 6-73970 |

[51] Int. Cl.$^6$ .................................................. A61B 17/00
[52] U.S. Cl. ........................ 606/205; 606/170; 606/174; 606/180; 128/751
[58] Field of Search .................... 606/51, 52, 174, 606/205–211; 604/22; 128/750–755

[56] References Cited

U.S. PATENT DOCUMENTS

| 4,483,562 | 11/1984 | Schoolman | 606/174 |
| 4,643,190 | 2/1987 | Heimberger . | |
| 4,782,833 | 11/1988 | Einhorn et al. . | |
| 4,872,456 | 10/1989 | Hasson . | |
| 5,254,130 | 10/1993 | Poncet et al. . | |
| 5,275,614 | 1/1994 | Haber et al. . | |
| 5,281,230 | 1/1994 | Heidmueller . | |
| 5,287,845 | 2/1994 | Faul et al. . | |
| 5,443,479 | 8/1995 | Bressi, Jr. | 606/208 |
| 5,454,827 | 10/1995 | Aust et al. | 604/174 |
| 5,540,706 | 7/1996 | Aust et al. | 606/170 |

FOREIGN PATENT DOCUMENTS

| 0134251 | 3/1985 | European Pat. Off. . |
| 0 216 532 | 4/1987 | European Pat. Off. . |
| 0537574 | 4/1993 | European Pat. Off. . |
| 0543107 | 5/1993 | European Pat. Off. . |
| 0 565 049 | 10/1993 | European Pat. Off. . |
| 36 32 786 | 3/1988 | Germany . |
| 92 07 414.6 | 10/1992 | Germany . |
| 41 14 311 | 11/1992 | Germany . |
| 2-46327 | 12/1990 | Japan . |
| 5-76413 | 10/1993 | Japan . |
| 2189735 | 11/1987 | United Kingdom . |
| WO94/00059 | 1/1994 | WIPO . |

*Primary Examiner*—Michael Buiz
*Assistant Examiner*—William Lewis
*Attorney, Agent, or Firm*—Burns, Doane, Swecker & Mathis, LLP

[57] ABSTRACT

A surgical instrument is disclosed which is suitably adapted for use in operations to be performed under an endoscopic surgery. This surgical instrument comprises an elongate main body of the instrument, a leading end part disposed on the leading end side of the main body of the instrument and endowed with surgically operating member for producing an open-close motion or a rotary motion, a manipulating part for effecting remote control of the surgically operating member, and an elongate transmitting member for transmitting the operation in the manipulating part to the leading end part mentioned above. It is provided in or near the leading end part with a locking mechanism for regulating the motion of the transmitting member relative to the leading end part and fixing the posture of the surgically operating member. This surgical instrument allows the surgically operating member to fix the posture thereof infallibly, permits simplification of the construction of the manipulating part, and enjoys outstanding operational efficiency.

18 Claims, 19 Drawing Sheets

SURGICAL INSTRUMENT

BACKGROUND OF THE INVENTION

1. Field of the Invention

This invention relates to surgical instruments such as, for example, forceps and scissors, and more particularly to surgical instruments ideally adapted for operations to be performed under an endoscopic surgery.

2. Description of the Prior Art

A forceps so constructed as to effect remote control of a grasping mechanism disposed at the leading end thereof with a manipulating part disposed on the basal end side thereof has been known (JA-Y2-02-46,327, JA-U-05-76,413, etc.). Specifically, this forceps is provided at the leading end thereof with a grasping mechanism consisting of a pair of open-close claw member and at the basal end part of a transmission shaft connected to the grasping mechanism with claw manipulating means consisting of a stationary grasping part and a rotary grasping part rotatable toward and away from the stationary grasping part, whereby a rotation of the rotary grasping part induces traction of a transmitting lever built in the transmission shaft in the longitudinal direction so as to open or close the claw member. Either of the stationary grasping member and the rotary grasping member is provided with a ratchet member and the remaining member with an engaging member adapted to be meshed with the teeth of the ratchet member. In this mechanism by adjusting the position of engagement between the ratchet member and the engaging member, the opening angle of the rotary grasping part relative to the stationary grasping member is set as desired and, consequently, the opening angle of the two claw members of the grasping mechanism is fixed.

Incidentally, regarding the excision of the appendix and the gallbladder, the operation performed under an endoscopic surgery and obviating the necessity for laparotomy has been attracting attention in recent years as a prospective alternative to the conventional laparotomy. This operation under an endoscopic surgery is implemented by inserting four trocars, for example, through the abdominal wall into the abdominal cavity, displaying on a monitor screen the image of the interior of the abdominal cavity with the aid of a miniature camera inserted via one of the trocars, and enabling the surgeon to study the image on the screen and perform a desired surgical treatment by manipulating suitably a forceps, a scissors, and an electric scalpel inserted via the other trocars.

In this operation under an endoscopic surgery, the trocars which are straight tubes are inserted through the abdominal wall and fixed thereto. For the sake of protecting the tissue of the pierced part, the angle which the trocars form with the abdominal wall cannot be substantially varied. As a result, the forceps, the scissors, and the electric scalpel are allowed to produce surgical treatments in only limited areas.

For the solution of this problem, it has been proposed to enlarge the area to be covered by the grasping mechanism at the leading end of the forceps by adapting the forceps to produce a bend or a curve in the leading end part of the elongate main body (transmission shaft) thereof after the forceps has been inserted through the trocar thereby allowing the bend or the curve to be utilized in combination with the rotation of the forceps.

The conventional forceps described above, however, premises use of a rectilinear transmission shaft defying deformation and essentially requires a ratchet mechanism (a ratchet member and an engaging member) for fixing the opening angle of the two claw members of the grasping mechanism to be disposed in the handle manipulating part near the operator's hand. If the transmission shaft is adapted to produce a bend or a curve the conventional forceps will entail the following problem.

In the first place, when the transmission shaft is bent or curved, the tension of the transmitting lever built in the transmission shaft is proportionately varied and the opening angle of the two claw members and the grasping force of the forceps are inevitably varied possibly to the extent of hindering relevant surgical treatments. This problem is not limited to the case of bending or curving the transmission shaft. It originates also in the elongation of the transmitting level and the play and the backlash of the claw manipulating means owing to changes in ambient conditions and material characteristics. In the second place, since the handle manipulating part is provided with a mechanism for fixing the opening angle of the forceps and a leaf spring for urging the rotary grasping part, these accessorial components possibly obstruct the manipulation of the handle and jeopardize the convenience of manipulation and, at the same time, complicate the construction of the forceps.

SUMMARY OF THE INVENTION

An object of this invention is to provide a surgical instrument which permits infallible fixation of surgically operating means, simplifies the construction of a manipulating part, and excels in the convenience of manipulation.

To accomplish the object described above, this invention provides a surgical instrument comprising an elongate main body of the instrument, a leading end part disposed on the leading end side of the main body and provided with surgically operating means for producing an open-close motion or a rotary motion, a manipulating part disposed on the basal end side of the main body and adapted to effect remote control of the surgically operating means, and an elongate transmitting member adapted to transmit the operation at the manipulating part to the leading end part and having provided at or near the leading end part a locking mechanism for regulating the motion imparted by the transmitting member on the leading end part and fixing the posture of the surgically operating means.

The invention will be better understood and the objects, features, and advantages thereof other than those set forth above will become apparent when consideration is given to the following detailed description thereof, which makes reference to the annexed drawings.

DETAILED DESCRIPTION OF THE PREFERRED EMBODIMENT

Figure 1:
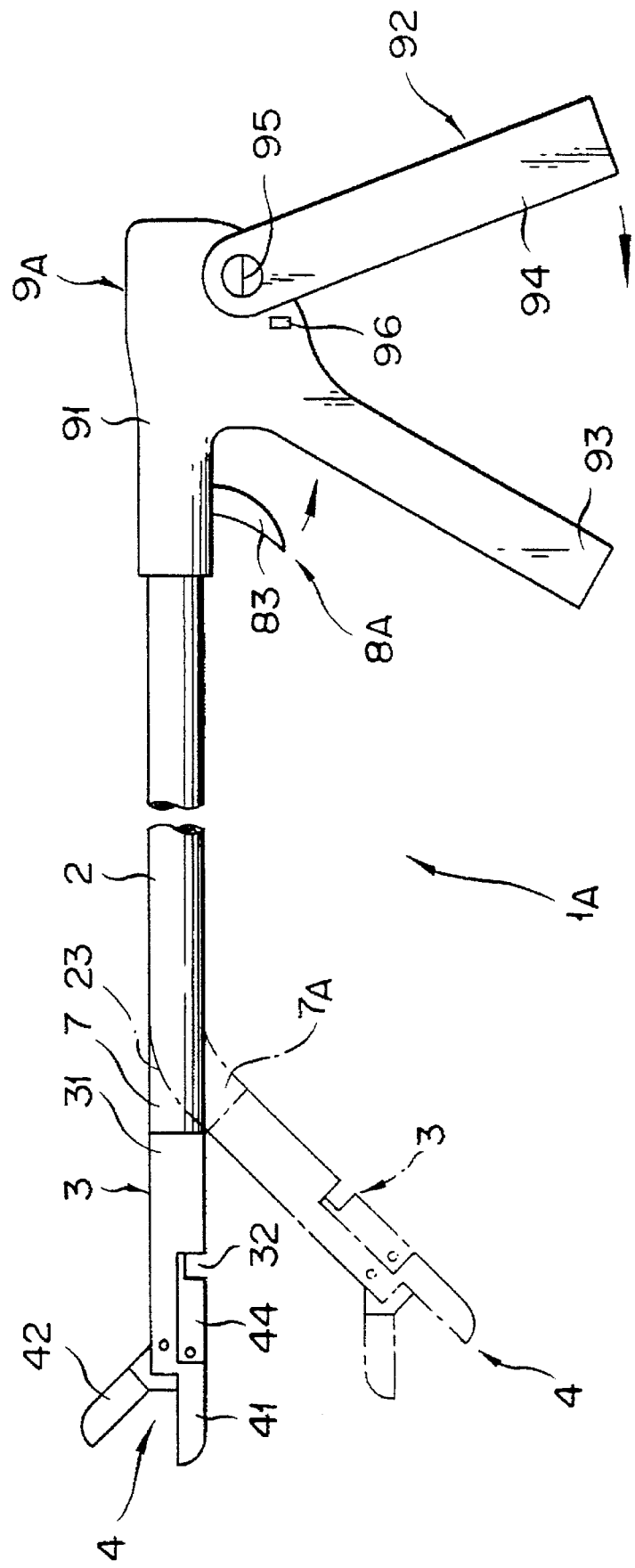
FIG. 1 is an overall side view illustrating a first embodiment of the surgical instrument according to this invention.

Now, the surgical instrument of this invention will be described in detail below based on the preferred embodiments which are illustrated in the annexed drawings. In the following description, the right side in a diagram will be referred to as "basal end" and the left side as "leading end."

A surgical instrument (forceps) 1A of a first embodiment of this invention illustrated in FIGS. 1 through 4 is mainly used for an operation under an endoscopic surgery and is composed of an elongate main body 2, a leading end part 3 disposed on the leading end side of the main body 2 and provided with surgically operating means 4 for producing an open-close motion or a rotary motion, a manipulating part 9A disposed on the basal end side of the main body 2, an elongate transmitting member 6 adapted to interconnect the leading end part 3 and the manipulating part 9A, locking means 7A disposed in the leading end part 3 (or the vicinity thereof), and unlocking means 8A for relieving the locking means 7A of a locked state.

Now, these component elements of the surgical instrument will be described successively below.

The main body 2 of the instrument is a hollow elongate member having formed therein an empty space 21 capable of storing the transmitting member 6 and is provided at the leading end thereof with a screwed part 22 to be helically meshed with the leading end part 3.

Figure 2:
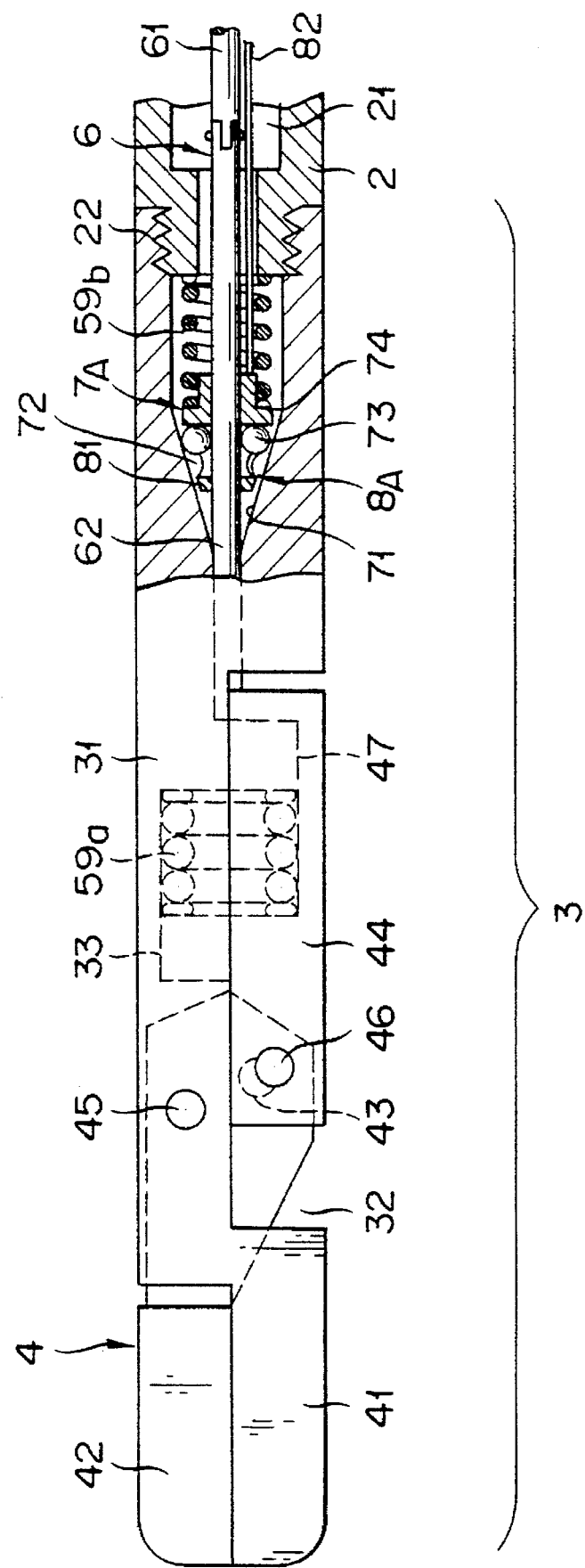
FIG. 2 is a partially sectioned side view illustrating as magnified the construction near the leading end part of the surgical instrument shown in FIG. 1.

The shape of the lateral cross section of the main body 2 of the instrument is not particularly limited but may be a circle, an ellipse, a polygon, etc. When it has a circle for the lateral cross section thereof as illustrated in FIG. 2, the outside diameter of the main body 2 is such that the main body 2 may be inserted in a trocar. To be specific, the outside diameter of the main body 2 is desired to be in the approximate range of from 5 to 18 mm.

In the construction illustrated in the diagram, the main body 2 of the instrument is depicted in a rectilinear shape in consideration of the insertion thereof into the trocar. It does not need to be limited to the rectilinear shape but may be curved or bent beforehand in a desired shape.

Otherwise, the main body 2 may be provided with at least one curving part 23 which is capable of being bent in a desired shape as will be specifically described hereinbelow. When this construction is adopted, the area in which the surgically operating means 4 is allowed to produce a surgical treatment on the vital tissue is enlarged and the surgically operating means 4 is enabled to assume a more proper posture in producing the surgical treatment.

The transmitting member 6 is composed of a linear part 61 and a barlike connecting member 62 connected to the leading end of the linear member 61. The linear member 61 is desired to be vested with flexibility (enough to permit curvature) throughout the entire volume thereof or in part thereof. For the linear member 61 metal wires such as of stainless steel, tungsten, carbon steel, and superelastic alloy, wires formed of fibers of polymer materials such as polyamides (totally aromatic polyamides), polyesters, ultramacromolecular poly-ethylene, and carbon fibers which withstand relatively high tension (hereinafter referred to as "high-tension fibers"), aggregates of such elementary wires, and other composites thereof may be used.

As the linear member 61 of an aggregate of component wires, a cord obtained by winding at least one component wire or a plurality of component wires of similar or dissimilar kind in a set direction round at least one component wire (particularly a metal wire) (in the pattern of a coil, for example) and further winding thereon at least one same or different component wire in the direction opposite to the set direction mentioned above can be advantageously used. The linear member of this construction is at an advantage in excelling in the ability to follow the motion of traction produced in the manipulating part 9A and curbing the variation (distortion) of the length due to a twist or a bend.

Though the outside diameter of this linear member 61 is not particularly limited, it is desired in the present embodiment to be in the approximate range of from 1.0 to 2.5 mm, preferably from 1.0 to 1.5 mm.

As concrete examples of the material for the formation of the connecting member 62, metallic materials such as aluminum, brass, copper, stainless steel, tungsten, carbon steel, and superelastic alloy, relatively hard resins such as polycarbonate, polyethylene, polypropylene, hard polyvinyl chloride, and polyester, and high-tension fibers mentioned above may be cited.

The leading end of this connecting member 62 is inserted into the leading end part 3 and then connected to or joined with the basal end of a slider 44 which will be specifically mentioned hereinafter. Though the shape of the cross section of the connecting member 62 is not particularly limited, it may be a circle, an ellipse, a rectangle, a hexagon, and other polygon, for example.

Figure 3:
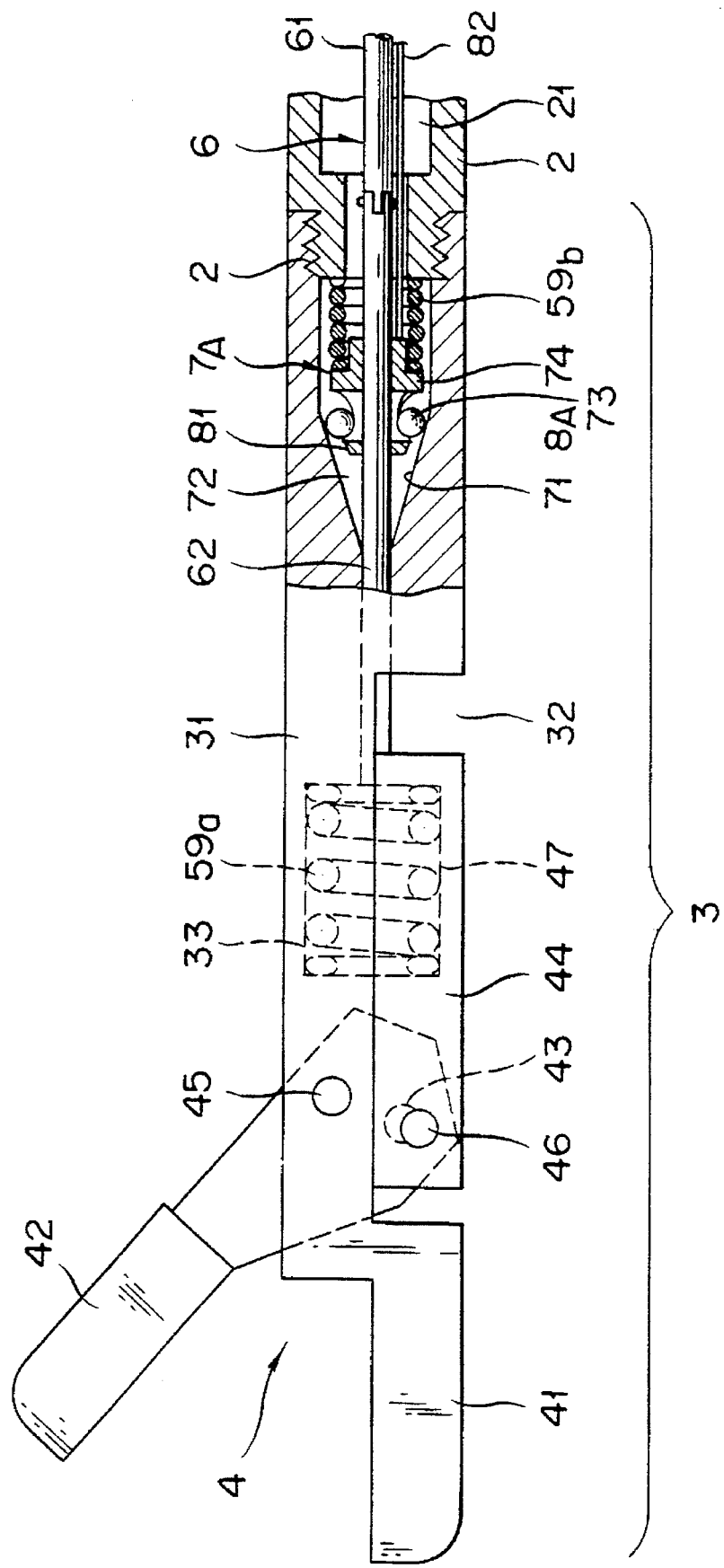
FIG. 3 is a partially sectioned side view illustrating as magnified the construction near the leading end part of the surgical instrument shown in FIG. 1.

The leading end part 3 is provided, as illustrated in FIG. 2 and FIG. 3, with the surgically operating means 4, urging means formed of a first coil spring 59a, and part of the unlocking means 8A.

The surgically operating means 4 forms a grasping mechanism capable of nipping vital tissue. This means 4 is provided with a pair of open-close members one of which is driven relative to the other to produce an open-close motion, i.e. a stationary nipping piece 41 and a movable nipping piece 42 which is opened or closed relative to the stationary nipping piece 41. The movable nipping piece 42 is attached in the basal end part thereof revolvably to the main body 31 of the leading end part by means of a pin 45.

The main body 31 of the leading end part has a notch 32 formed in the lower part in FIG. 2. Inside this notch 32, the slider 44 which is slidable in the longitudinal direction of the leading end part 3 is disposed. A pin 46 is projected from the leading end part of the slider 44. This pin 46 is inserted into an oblong hole 43 formed in the lower part of the basal end of the movable nipping piece 42.

Owing to this construction, the stationary nipping piece 41 and the movable nipping piece 42 assume a closed state (in the state shown in FIG. 2) when the transmitting member 6 is drawn toward the basal end side by the manipulation of the handle of a handle part 92 which will be specifically mentioned hereinbelow and the slider 44 is consequently positioned on the basal end side within the notch 32. When the grasping force of the handle part 92 is alleviated or removed and, consequently, the transmitting member 6 is moved toward the leading end side and the slider 44 is moved toward the leading end side inside the notch 32, then the pin 46 depresses the inner wall surface of the oblong hole 43 and the movable nipping piece 42 revolves round the pin 45 as the center to open the movable nipping piece 42 (the state shown in FIG. 3).

Optionally, the oblong hole 43 may be omitted and, instead, the slider 44 may be adapted so as to be deformed in consequence of a motion of itself and consequently enabled to absorb the motion of the pin in the vertical direction in FIG. 2.

The first coil spring 59a is accommodated in a compressed state inside a recess 33 formed in the main body 31 of the leading end part and a recess 47 formed in the slider 44. The first coil spring 59a is urging means, which by virtue of the elastic force thereof, urges the slider 44 toward the leading end thereof, namely in the direction of opening the movable nipping piece 42. Since the present embodiment has the first coil spring 59a as urging means built in the leading end part 3 as described above, it is not required, unlike the conventional forceps mentioned above, to be provided in the handle part 92 as with a leaf spring capable of urging a movable handle 94 in the opening direction thereof. The construction of the manipulating part 9A is simplified and the operating property thereof improved.

The locking means 7A serves the purpose of inhibiting the motion of the transmitting member 6 in the longitudinal direction thereby fixing the posture of the surgically operating means 4, namely the opening angle of the movable nipping piece 42.

The locking means 7A, as illustrated in FIG. 2 and FIG. 3, is provided with a ball accommodating part 72 having a tapered inner wall surface 71 whose inner diameter gradually decreases toward the leading end thereof. The connecting member 62 axially penetrates the ball accommodating part 72. A plurality of balls 73 are disposed inside the ball accommodating part 72 and around the connecting member 62. In the basal end part of each of the balls 73, a depressing member 74 as means to depress the balls 73 toward the leading end side of the ball accommodating part 72 and a second coil spring 59b (urging means) for urging the depressing member 74 toward the leading end are disposed.

The present embodiment, unlike the conventional forceps, is not required to be provided in the handle part 92 thereof with a ratchet mechanism because it has the locking means 7A built in the leading end part 3 as described above and, therefore, is enabled to simplify the construction of the manipulating part 9A and improve the operating property thereof because it suffers no degradation of operational accuracy due to backlash or play. Further, it enables the opening angle of the stationary nipping piece 41 and the movable nipping piece 42 and the grasping force thereof to be fixed even when the linear member 61 is stretched because of a change in the tension thereof due to a bend or a curve of the main body 2 of the instrument.

To the leading end of the depressing member 74 is connected or joined a colliding member 81 which is adapted to collide against the balls 73 and move them toward the basal end side. To the basal end of the depressing member 74 is connected the leading end of a wire 82 which is formed of the aforementioned metallic cords or high-tension fibers and is intended to draw the depressing member 74 and the colliding member 81 toward the basal end side. The wire 82 passes through the empty space in the main body 2 of the instrument. The basal end of the wire 82 is connected to an unlocking lever (unlocking member) 83 disposed in the manipulating part 9A which will be specifically mentioned hereinbelow. The colliding member 81, the wire 82, and the unlocking lever 83 jointly form the unlocking means 8A which cancels the inhibition laid by the locking means 7A on the motion of the transmitting member 6 in the longitudinal direction. The wire 82 may have an outside diameter in the approximate range of from 0.3 to 1 mm.

Figure 5:
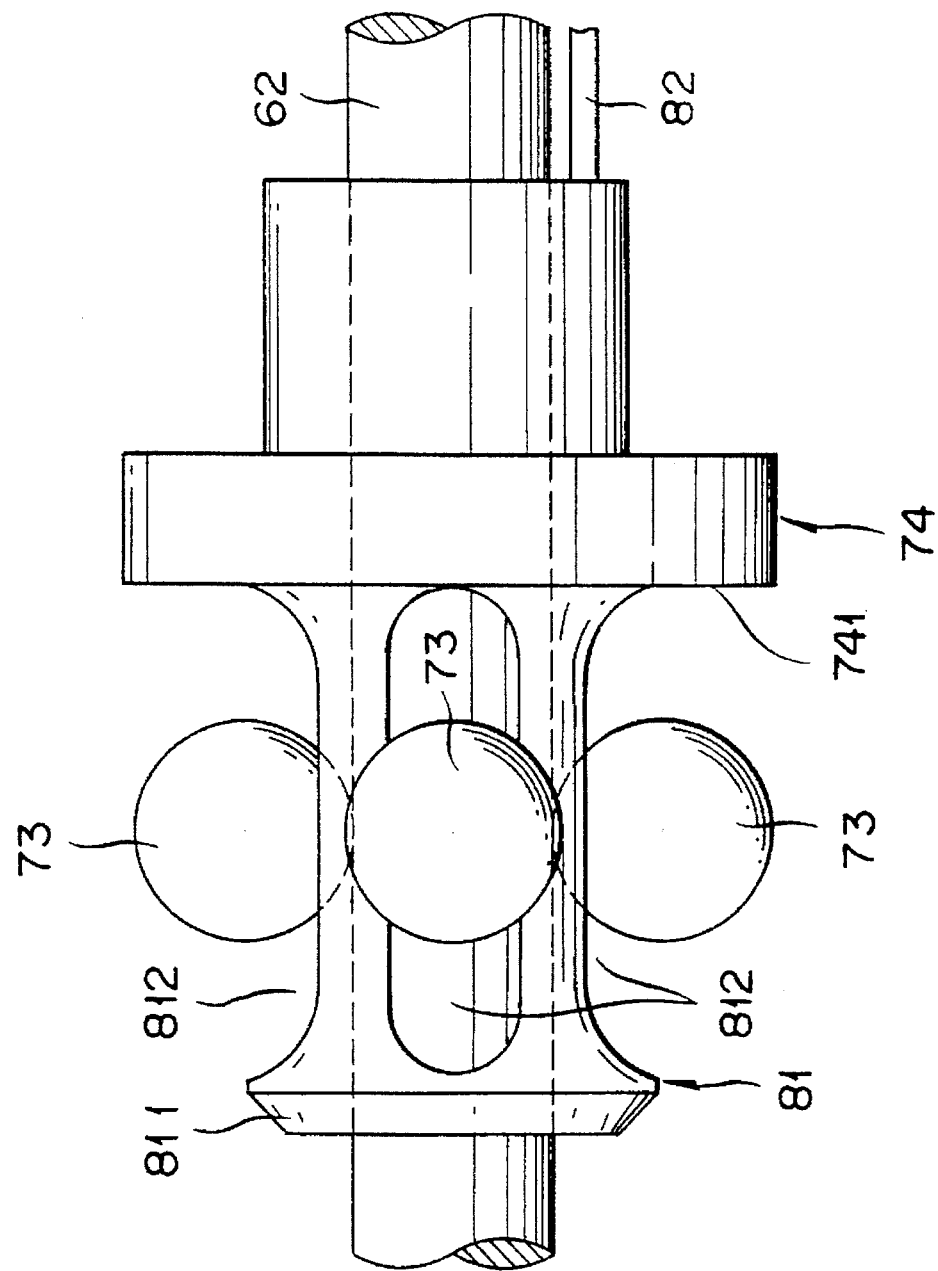
FIG. 5 is a side view illustrating as magnified the construction of a pressing member and a colliding member of the first embodiment.

The colliding member 81, as illustrated in FIG. 5, is a substantially cylindrical member which is provided at the leading end thereof with a head 811 and on the peripheral part between the head 811 and a leading end surface 741 of the depressing member 74 with a plurality of slots 812 extended in the axial direction of the transmitting member 6. The balls 73 are disposed one each inside these slots 812.

The balls 73 made of varying metal or hard resin, for example, are advantageously used. The diameter of these balls 73 and the number of the balls to be disposed are not particularly limited. In the case of the present embodiment, it is desirable to have disposed around the connecting member 62 about four to six balls having a diameter in the approximate range of from 1.0 to 1.6 mm.

When the depressing member 74 urged toward the leading end thereof by the elastic force of the second coil spring 59b as illustrated in FIG. 2 depresses the balls 73 in the same direction, the balls 73 collide against the tapered inner wall surface and, in consequence of the reaction, generate a depressing force toward the axis, depress themselves against the inner wall surface of the connecting member 62, and come to rest thereon. In consequence of the series of actions thus produced, the connecting member 62 produces a friction force with the balls 73 and inhibits the transmitting member 6 from moving in the longitudinal direction (hereinafter referred to as "locked state").

At this time, the opening angle of the movable nipping piece 42 can be fixed at a desired value in accordance with the length to which the transmitting member 6 is forced out. In the construction illustrated in FIG. 2, the state in which the length of the motion of the transmitting member 6 toward the leading end is smallest, namely the state in which the movable nipping piece 42 is closed (opening angle=0), is retained. This locked state is obtained simply by stopping the manipulation of the handle part 92 which will be specifically mentioned hereinbelow without requiring any special locking operation. The insertion of the leading end part 3 and the main body 2 of the instrument into the relevant trocar, therefore, can be easily attained by closing the movable nipping piece 42 by the manipulation of the handle part 92 and thereafter making the insertion into the trocar without reference to retention, relaxation, or removal of the grasping force exerted on the handle part 92.

When the wire 82 is drawn toward the basal end against the elastic force of a second coil spring 59b by the manipulation of the unlocking lever 83 which will be mentioned hereinbelow, the depressing member 74 and the colliding member 81 are moved toward the basal end, the head 811 of the colliding member 81 is consequently caused to collide against the balls 83, and the balls 73 are moved under pressure toward the basal end as illustrated in FIG. 3. As a result, the pressing force exerted by the balls 73 on the peripheral surface of the connecting member 62 decreases or vanishes, the connecting member 62 moves toward the leading end side under the urging force of the first coil spring 59a, and the movable nipping piece 42 completely opens.

Incidentally, the locking means 7A constructed as illustrated may be disposed inside the main body 2 of the instrument and near the leading end part 3 (on the leading end side of the curving part 23 when the main body 2 of the instrument is adapted to produce a bend or a curve).

Figure 4:
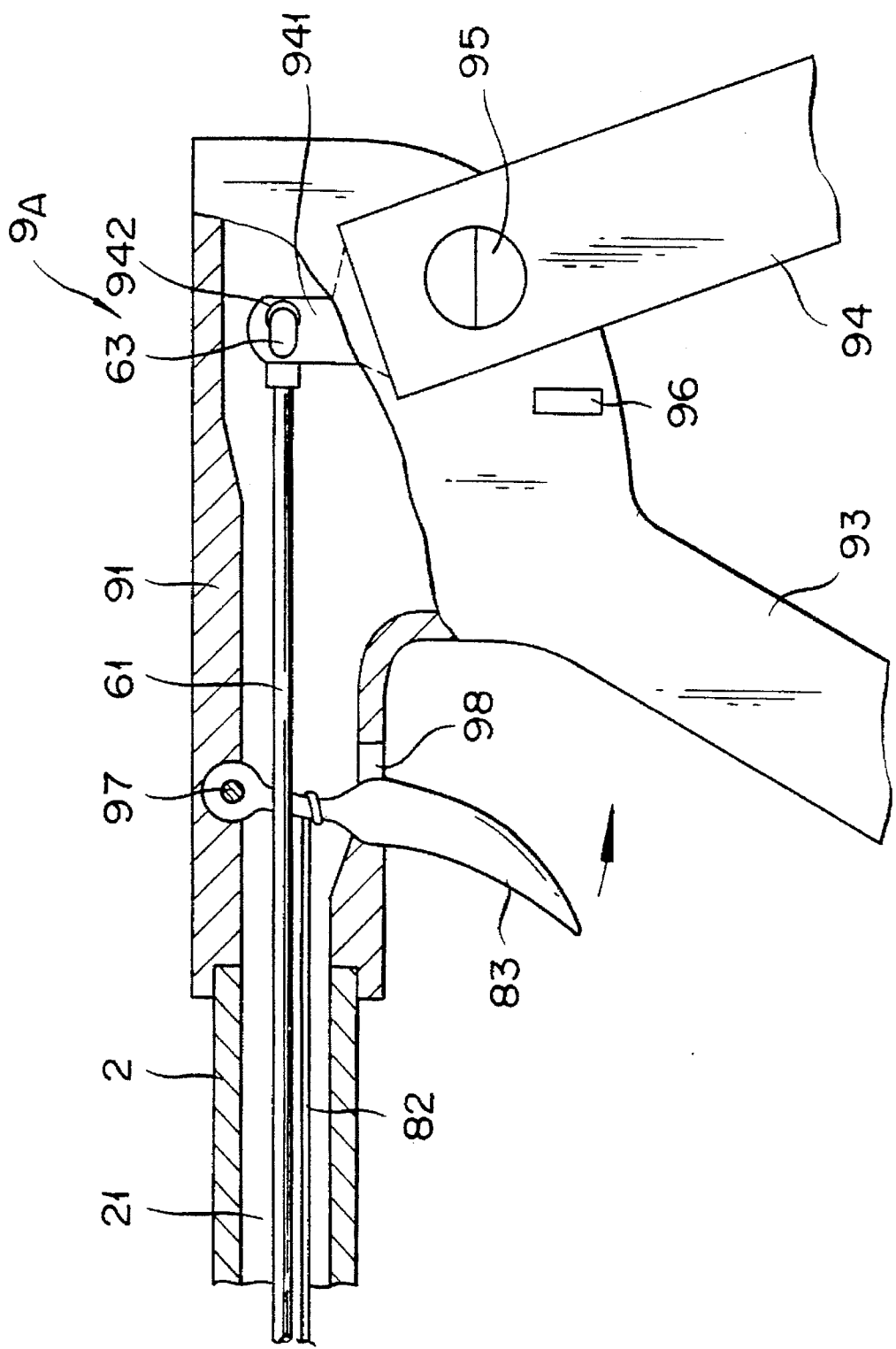
FIG. 4 is a partially sectioned side view illustrating as magnified the construction near the basal end part of the surgical instrument shown in FIG. 1.

The main body 2 of the instrument, as illustrated in FIG. 1 and FIG. 4, is provided on the basal end side thereof with the manipulating part 9A for opening and closing the surgically operating means 4 by remote control. This manipulating part 9A is composed of a stationary handle 93 provided stationarily or integrally on a main body 91 of the manipulating part and the movable handle 94 to be opened and closed relative to the stationary handle 93.

The movable handle 94 is revolvably attached to the main body 91 of the manipulating part at the upper end part in the diagram by means of a shaft member 95. The movable handle 94, as illustrated in FIG. 4, is provided in the upper part thereof with a protruding piece 941 which is inserted into the main body 91 of the manipulating part. The linear member 61 is fixed by causing a hook 63 fixed to the basal end of the linear member 61 to be hooked in a hole 942 formed in the upper end part of the protruding piece 941.

When the handle part 92 is gripped and the movable handle 94 is revolved in the direction indicated by an arrow in FIG. 1, the protruding piece 941 is revolved clockwise in FIG. 4 around the shaft member 95 and the linear member 61 is drawn toward the basal end side and the movable nipping piece 42 held thence in the opened state is closed. When the grip on the handle part 92 is removed or relaxed while the locking means 7A is not in an active state, the linear member 61 is moved toward the leading end side by the urging force of the first coil spring 59a and the movable nipping piece 42 is turned to the home position (the position shown in FIG. 1).

Then, from the outer surface of the lower part of the main body 91 of the manipulating part, a stopper 96 for engaging itself firmly on the movable handle 94 and regulate the range of revolution thereof is projected. By this arrangement, the otherwise possible breakage of the transmitting member 6 due to the exertion of unduly large grasping force on the handle part 92 can be prevented.

The position of the stationary handle 93 and the movable handle 94 may be reversed.

On the leading end side of the main body 91 of the manipulating part, the unlocking lever 83 for effecting traction of the wire 82 is disposed. Specifically, a pin 97 is suspended inside the upper part of the leading end side of the main body 91 of the manipulating part and the unlocking lever 83 is revolvably supported in the upper end part thereof by the pin 97. The lower end side of the unlocking lever 83 protrudes from an opening 98 which is formed in the lower part on the leading end side of the main body 91 of the manipulating part. As a result, the unlocking lever 83 is allowed to revolve within the interior of the opening 98. The basal end part of the wire 82 is tied and fixed to the unlocking lever 83 at a point falling halfway along the length thereof. When the unlocking lever 83 is drawn toward the basal end side by the index finger of a user's hand gripping the handle part 92, for example, the wire 82 is drawn toward the basal end side and, as a result, the locked state formed by the locking means 7A is cancelled and the movable nipping piece 42 is completely opened as described above. When the index finger is removed from the unlocking lever 83, the wire 82 is moved toward the leading end side by the urging force of the second coil spring 59b and the unlocking lever 83 is returned to the home position (the position shown in FIG. 4).

Figure 6:
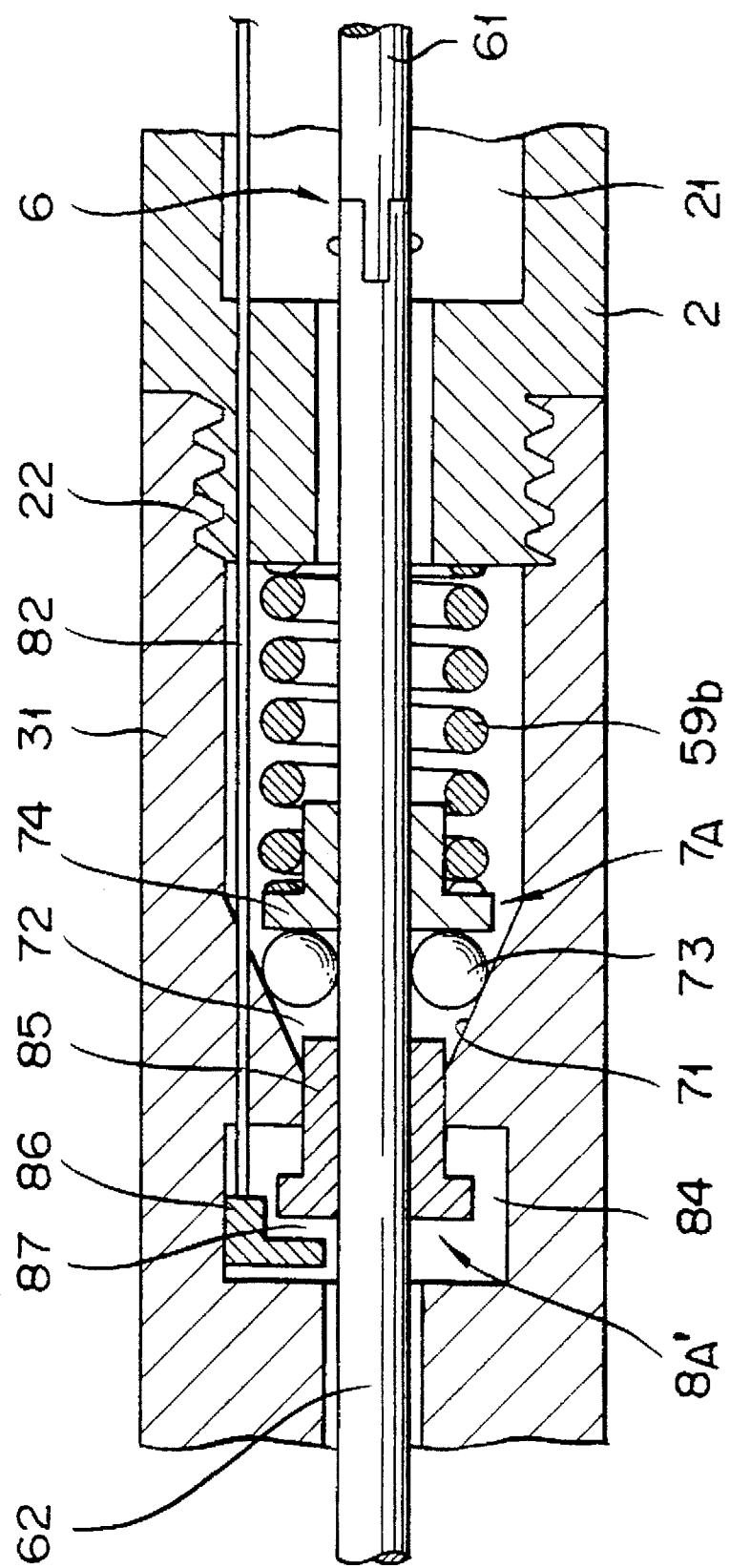
FIG. 6 is a partially sectioned side view illustrating another example of the construction of unlocking means of the first embodiment.

FIG. 6 is a partially sectioned side view illustrating another example of the construction of the unlocking means. As shown in this diagram, in the leading end side part of the main body 31 of the leading end part past the ball accommodating part 72, an unlocking member accommodating chamber 84 is formed. The unlocking member accommodating chamber 84 accommodates therein a tubular colliding member 85 pierced with the connecting member 62 and a hooked engaging member 86 for engagement with the leading end of the colliding member 85. The colliding member 85 in this case is so constructed that the depth of insertion thereof into the ball accommodating part 72 may be varied as the basal end part thereof is inserted into the ball accommodating part 72 and moved in the axial direction therein.

Though the engaging member 86 is allowed to contact the colliding member 85, it is desired to be opposed thereto through a stated gap 87 as illustrated in the diagram. Then, the leading end of the wire 82 is connected in the same manner as mentioned above to the engaging member 86 and the basal end of the wire 82 is connected also in the same manner as mentioned above to the unlocking lever 83. The colliding member 85, the engaging member 86, the wire 82, and the unlocking lever 83 jointly form an unlocking means 8A' which cancels the locked state formed by the locking means 7A.

When the wire 82 is drawn toward the basal end side by the manipulation of the unlocking lever 83, the engaging member 86 is moved toward the basal end side and made to collide against the colliding member 85. When the wire 82 is further drawn toward the basal end side against the elastic force of the second coil spring 59b, the engaging member 86 and the colliding member 85 are moved toward the basal end side, with the result that the colliding member 85 will be made to collide against the balls 73 and the balls 73 will be moved under pressure toward the basal end side. As a result, the pressing force exerted by the balls 73 on the peripheral surface of the connecting member 62 either diminishes or vanishes and the connecting member 62 is moved toward the leading end side by the urging force of the first coil spring 59a and the movable nipping piece 42 is completely opened.

In the unlocking means 8A' constructed as described above, the colliding member 85 is driven independently of the depressing member 74 and, at the same time, enabled to give rise to the gap 87 and the gap between the basal end surface of the colliding member 85 and the balls 73. This arrangement infallibly prevents the erroneous operation of the unlocking means which is possibly caused when the tension of the wire 82 is varied by a bend or a curve formed in the main body 2 of the instrument.

Figure 7:
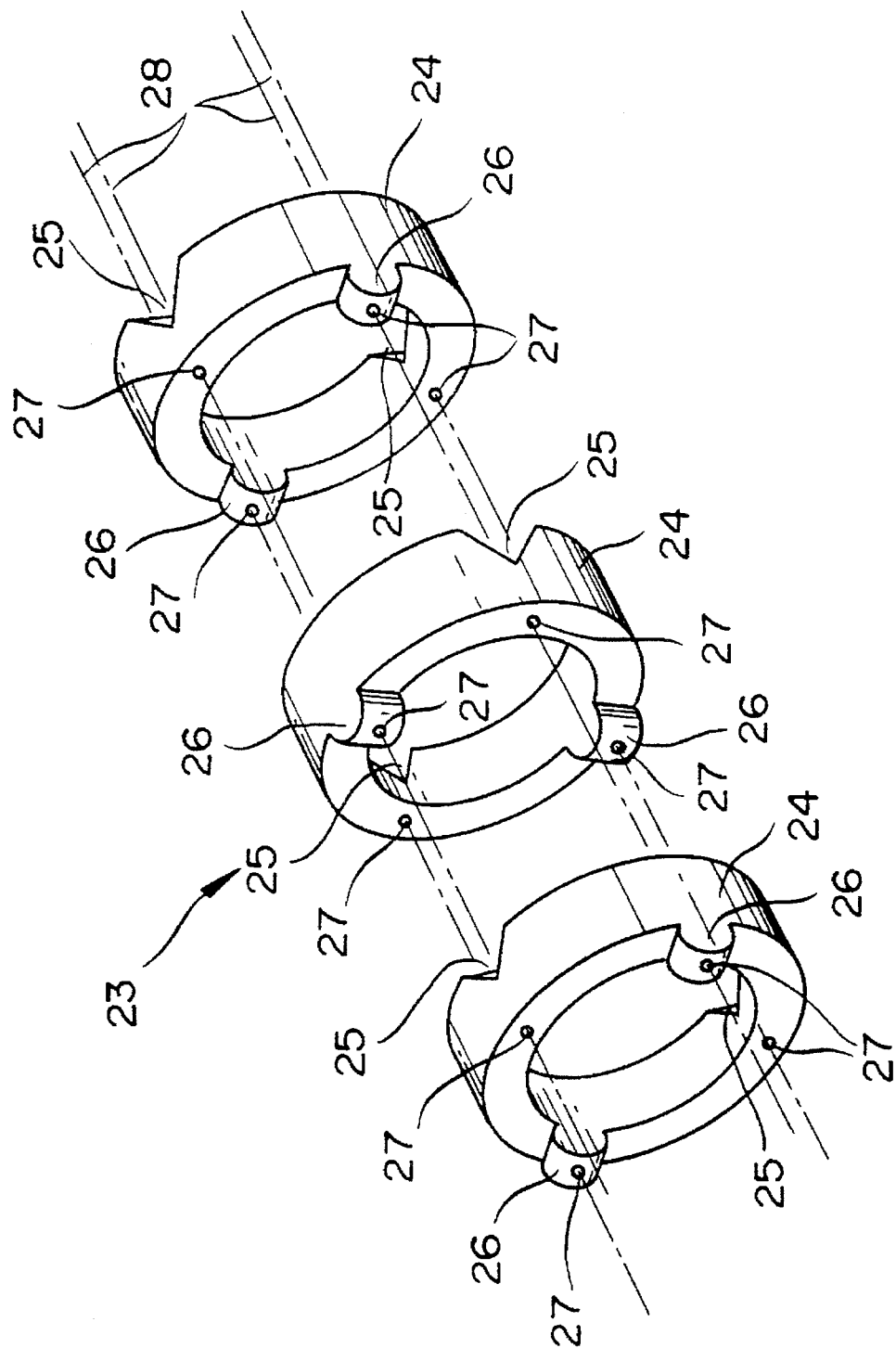
FIG. 7 is an exploded perspective view illustrating one example of a curved part of the first embodiment.

FIG. 7 is an exploded perspective view illustrating partially an example of the construction of the curving part 23 of the main body 2 of the instrument. The curving part 23, as illustrated in the diagram, is formed by joining a plurality of mutually revolvable joint rings 24. FIG. 7 depicts three joint rings 24. The number of these joint rings 24 does not need to be limited to three but may be in the approximate range of from 4 to 30.

On one of the opposite annular surfaces of each of the joint rings 24, one pair of V-shaped grooves 25 are formed and opposed to each other across the center of the joint ring 24. On the remaining annular surface of the joint ring 24, a pair of semicircular protuberances 26 opposed to each other across the center of the joint ring 24 are formed as deviated by 90° from the grooves 25. The adjacent joint rings 24 are so disposed that their grooves 25 may deviate from each other with an angle of 90° and the adjacent joint rings 24 are joined to each other so that the two protuberances 26 on one of the adjacent joint rings 24 may thrust into the two grooves 25 on the other joint ring 24.

Then, through holes 27 are formed one each at the positions of the opposite grooves 25 and the opposite protuberances 26 on each of the joint rings 24. The joint rings 24 may be assembled, when necessary, by inserting four flexible wires 28 through the coinciding through holes 27.

When the adjacent joint rings 24 are so positioned as to have the protuberances 26 on each joint ring inserted into the grooves 25 on the neighboring joint ring, the protuberances 26 are allowed to revolve inside the grooves 25 because of gaps formed one each between the adjacent joint rings 24. As a result, the adjacent joint rings 24 are revolved relative to one another. The angle of revolution between one set of adjacent joint rings 24 is small. When the angles of revolution obtained in the plurality of sets of adjacent joint rings 24 are summed, the total forms curvature (about 80° to 120°, for example) which the curved part as a whole is required to produce. In the present embodiment, it is in four, i.e. two vertical and two horizontal, directions on the cross section of the main body 2 of the instrument that the curvature is attained.

Optionally, the outer periphery of each of the joint rings 24 may be covered, though not illustrated in the diagram, with a layer which is formed of a material possessing elasticity or flexibility.

The curving part 23 constructed as described above may be adapted either to be actively bent or curved by the attraction of the lines 28 or to be passively bent or curved by virtue of external stress. Further, the directions and numbers (degree of freedom) of curvature are not particularly limited.

The construction of the curving part 23 does not need to be limited to what is illustrated in the diagram. It may be provided with a bellows tube or a flexible tube instead. It is also permissible to compose the main body of the instrument with a hard pipe on the leading end part side and a hard pipe on the basal end side and one or more shafts for connecting the two hard pipes in a rotatable manner. The main body thus obtained, therefore, has freedom of bending.

To use the surgical instrument 1A of this invention, the handle part 92 is first grasped in a hand and the movable handle 94 is then revolved as already described to close the movable nipping piece 42. The surgical instrument 1A in the ensuant state is passed into the trocar which has been preparatorily inserted through the abdominal wall. An endoscope (miniature camera) inserted through another trocar is manipulated to display an affected area under treatment on the monitor screen, with the displayed view kept under constant observation. The treatment of the affected area is implemented by drawing the unlocking lever 83 toward the basal end side with the index finger of a hand gripping the handle 92 and opening the movable nipping piece 42 completely and closing the movable handle 94 to a desired angle. After the treatment is completed, the handle part 92 is again grasped in the hand and the movable nipping piece 42 is closed and the surgical instrument 1A is extracted through the trocar.

FIGS. 8 through 13 illustrate a second embodiment of the surgical instrument according to this invention. In the diagrams, like parts found in the preceding examples of the construction are denoted by like reference numerals. The description of these parts will be omitted here to avoid repetition.

Figure 8:
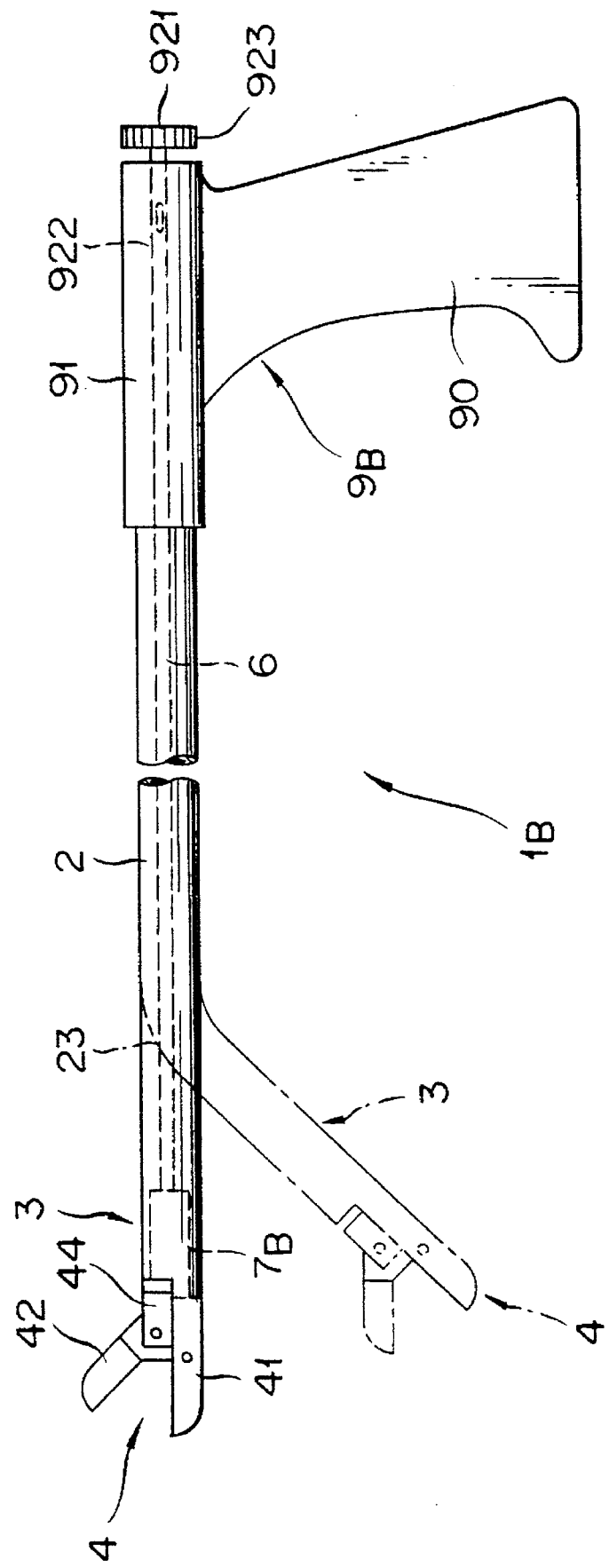
FIG. 8 is an overall side view illustrating a second embodiment of the surgical instrument of this invention.
Figure 9:
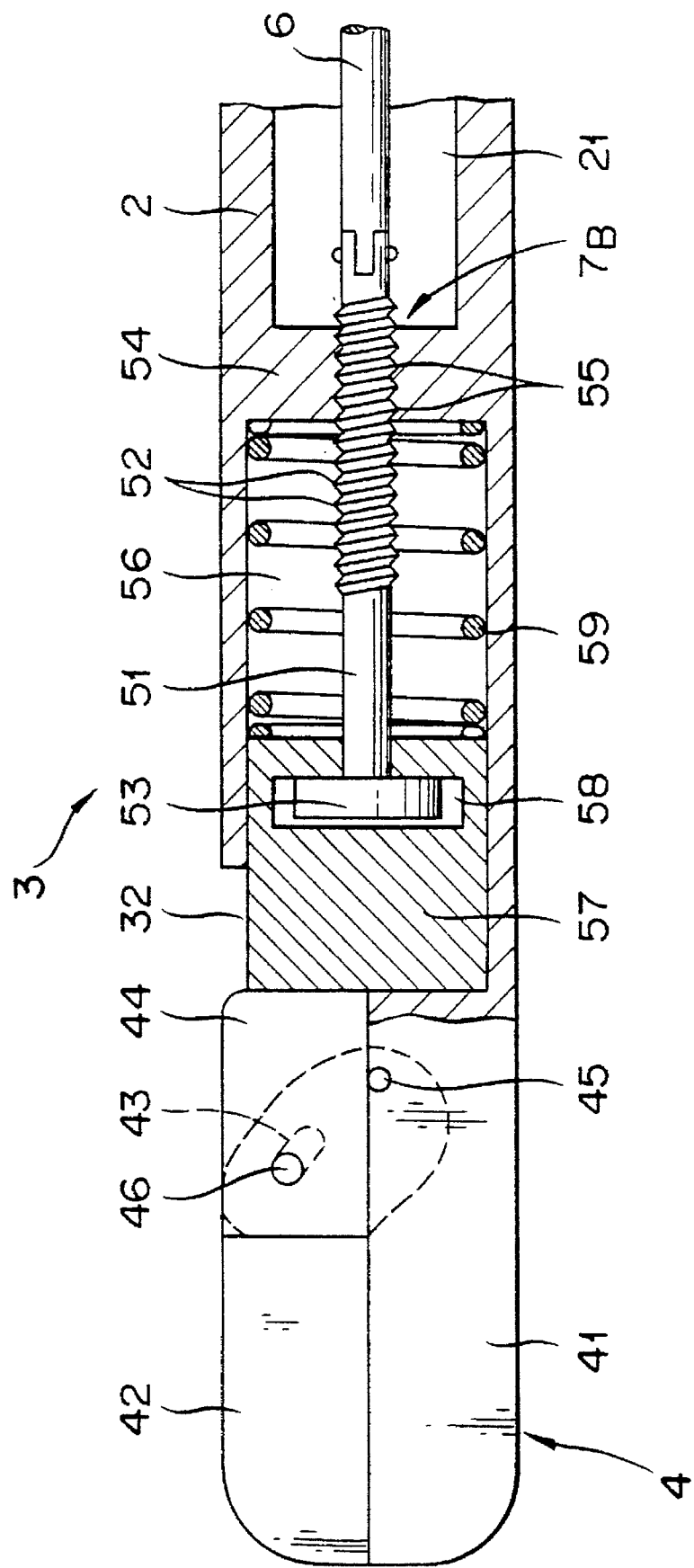
FIG. 9 is a partially sectioned side view illustrating as magnified the construction near the leading end part of the surgical instrument shown in FIG. 8.
Figure 10:
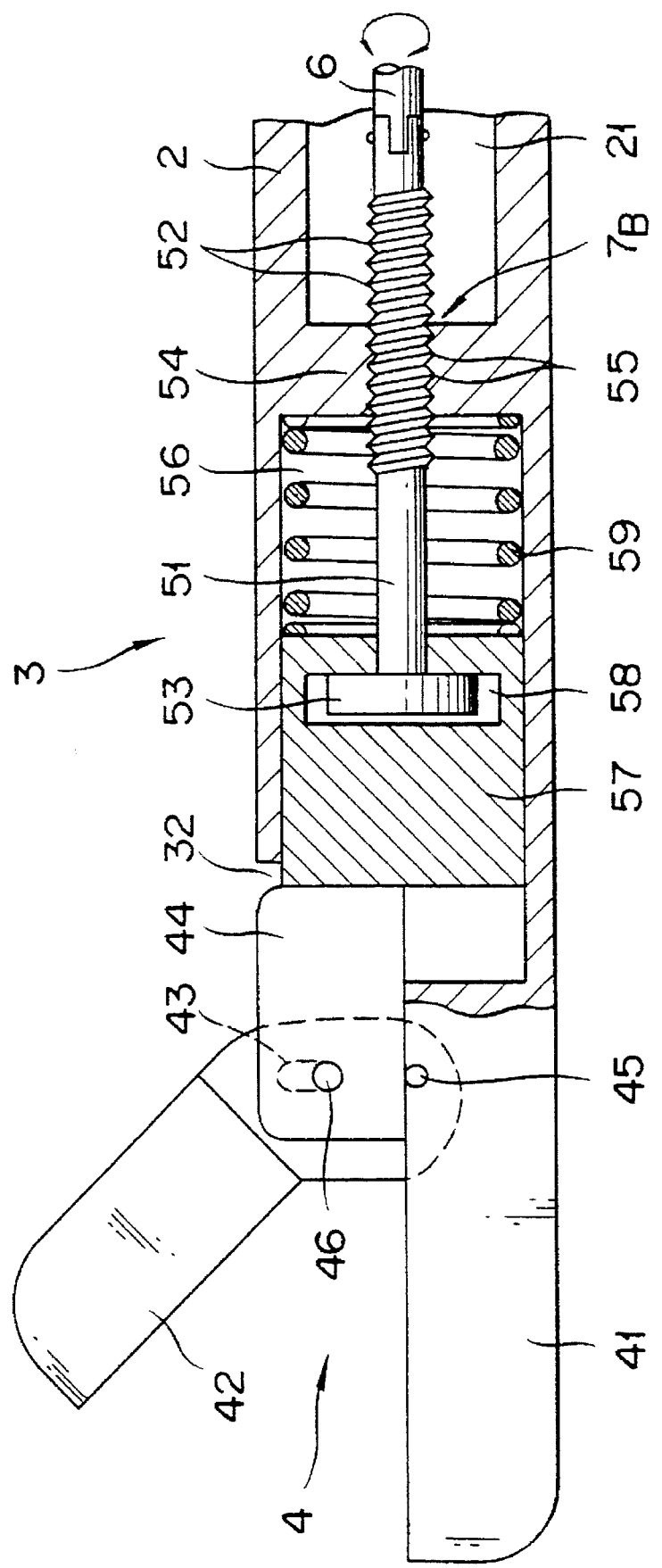
FIG. 10 is a partially sectioned side view illustrating as magnified the construction near the leading end part of the surgical instrument shown in FIG. 8.

A surgical instrument (forceps) 1B shown in FIGS. 8 through 10 is composed of an elongate main body 2 of the instrument, a leading end part 3 disposed on the leading end side of the main body 2 of the instrument, surgically operating means 4 disposed in the leading end part 3 and adapted to produce an open-close motion or a revolving motion, a manipulating part 9B disposed on the basal end side of the main body 2 of the instrument, an elongate transmitting member 6 disposed revolvably inside the main body 2 of the instrument and interconnecting the leading end part 3 and the manipulating part 9B, locking means 7B endowed with a function of converting the rotation of the transmitting member 6 into an open-close motion or a revolving motion of the surgically operating means 4 and serving to inhibit the motion of the transmitting member 6 in the longitudinal direction and fixing the posture of the surgically operating means 4, and a coil spring 59.

Now, these composing elements of the surgical instrument will be described successively hereinbelow.

The main body 2 of the instrument, as shown in FIG. 9, is a hollow elongate member having formed therein an empty space 21 capable of storing the transmitting member 6.

The transmitting member 6 is intended to transmit the revolving force of the manipulating part 9B and is desirably formed, either wholly or partly (particularly the portion which corresponds to the bending part 23 or the interior of a passage 901 shown in FIG. 13), of (bendable) linear members possessed of flexibility. The material and the outside diameter of this transmitting member 6 are equal to those of the linear member 61 and the connecting member 62 of the preceding embodiment.

As shown in FIG. 9 and FIG. 10, the surgically operating means 4 is disposed in the leading end part 3 and the locking means 7B for converting the rotation of the transmitting member 6 into an open-close motion or a revolving motion of the surgically operating means 4 and further locking the transmitting member 6 and the surgically operating means 4 are disposed between the surgically operating means 4 and the transmitting member 6.

The surgically operating means 4, similarly to that in the first embodiment described above, is provided with a stationary nipping piece 41 and a movable nipping piece 42. The movable nipping piece 42 is attached in the basal end part thereof revolvably to the basal part of the stationary nipping piece 41 by means of a pin 45.

A notch 32 is formed in the leading end part 3 in the upper part of the pin 45 in FIG. 9. Inside this notch 32 is disposed a slider 44 which is slidable in the longitudinal direction of the leading end part 3. A pin 46 is projected from the leading end part of the slider 44. This pin 46 is inserted into an oblong hole 43 formed in the upper part of the basal end of the movable nipping piece 42.

When the slider 44 is positioned on the basal end side inside the notch 32, the stationary nipping piece 41 and the movable nipping piece 42 are opened (in the state shown in FIG. 10). When the slider 44 is moved toward the leading end side inside the notch 32, the pin 46 depresses the inner wall surface of the leading end side of the oblong hole 43, the movable nipping piece 42 is revolved around the pin 45 as the center, and the movable nipping piece 42 is closed (in the state shown in FIG. 9).

Optionally, the oblong hole 43 may be omitted and, instead, the slider 44 may be adapted so as to be deformed in consequence of a motion of itself and consequently enabled to absorb the motion of the pin 46 in the vertical direction in FIG. 10.

The locking means 7B of the present embodiment is furnished with a function of converting the rotation of the transmitting member 6 into an open-close motion or a revolving motion of the surgically operating means 4 and a function of locking the transmitting member 6 and the surgically operating means 4. It is composed of a rotary shaft (revolving body) 51, a moving body 57 disposed on the leading end side of the rotary shaft 51, a first supporting part (counter body) 54 formed on the leading end side 3 of the main body 2 of the instrument, and an accommodating space 56 for the moving body 57. The basal end of the rotary shaft 51 is connected to the leading end of the transmitting member 6 and a spirally-shaped male screw 52 is formed midway on the periphery of the rotary shaft 51. On the supporting part 54 is formed a female screw 55 which is adapted to be meshed with the male screw 52 mentioned above. The rotary shaft 51 is supported on the supporting part 54 as held in the state in which the male screw 52 is meshed with the female screw 55.

In the leading end side part of the main body 2 of the instrument past the supporting part 54, the accommodating space 56 for accommodating the moving body 57 as held movably in the axial direction therein. The leading end side of this accommodating space 56 communicates with the notch 32 mentioned above.

The leading end of the moving body 57 is connected or joined to the slider 44. The rotary shaft 51 is rotatably connected to this moving body 57. Specifically, a disklike head 53 is attached fast to the leading end of the rotary shaft 51 and this head 53 is rotatably inserted into a disklike recess 58, for example, which is formed inside the moving body 57.

In the locking means 7B constructed as described above, when the rotary shaft 51 is rotated in a stated direction by the rotation of the transmitting member 6, the position of engagement between the male screw 52 and the female screw 55 is moved and the rotary shaft 51 is axially moved toward or away from the main body 2 of the instrument. As a result, the moving body 57 and the slider 44 is axially moved and the movable nipping piece 42 is opened or closed.

In the meantime, this locking means 7B does the substantial inhibition of the motion of the transmitting member 6 in the longitudinal direction by virtue of the engagement between the male screw 52 and the female screw 55 of the supporting part 54, with the result that the posture of the surgically operating means 4 or the opening angle of the movable nipping piece 42 will be fixed.

Now, the substantial inhibition of the motion signifies the completely inhibition of the movement or the permission of the movement to the indistinct extent that the posture of the surgically operating means 4 is not substantially changed, in the text.

Inside the accommodating space 56, the coil spring 59 as urging means for relieving the rotary shaft 51 and the moving body 57 of backlash (play between relevant parts) is accommodated in a compressed state between the basal end side inner wall of the accommodating space 56 and the basal end face of the moving body 57. By the elastic force of this coil spring 59, the moving body 57 is constantly urged toward the leading end side and the basal end face of the head 53 and the leading end side inner wall of a recess 58 are pressed tightly against each other. Thus, the possible backlash between these component parts is eliminated and the movable nipping piece 42 is enabled to produce an accurate open-close motion.

On the basal end side of the main body 2 of the instrument, the manipulating part 9B for effecting remote control of the open-close motion of the surgically operating means 4 is disposed as illustrated in FIG. 8. This manipulating part 9B is provided with a main body 91 of the manipulating part furnished with a handle part 90 and a disklike knob 921 rotatably supported on the basal end side of the main body 91 of the manipulating part. A rotary shaft 922 of the knob 921 is inserted into the main body 91 of the manipulating part and the leading end of this rotary shaft 922 is connected to the basal end of the transmitting member 6. On the periphery of the knob 921, a irregularity 923 for ensuring firm grip is formed in the axial direction.

In the manipulating part 9B so constructed, the handle part 90 is gripped in one hand and the knob 921 is manipulated by the other hand.

Now, the operation of the surgical instrument 1B of the present embodiment will be described hereinbelow.

When the knob 921 so held as to keep the movable nipping piece 42 in the opened state (the state shown in FIG. 10 is rotated in a stated direction, the rotating force thereof is transmitted via the rotary shaft 922 and the transmitting member 6 to the rotary shaft 51, with the result that the rotary shaft 51 will be rotated in the same direction. The rotary shaft 51 is consequently moved toward the leading end thereof and the moving body 57 and the slider 44 are moved toward the leading ends thereof. In consequence of this motion of the slider 44, the pin 46 presses the inner wall surface of the leading end side of the oblong hole 43 and the movable nipping piece 42 revolves round the pin 45 as the center and closes (the state shown in FIG. 9).

When the knob 921 is rotated in the direction opposite to the direction mentioned above, the rotary shaft 51 is rotated in the reverse direction. As a result, the rotary shaft 921 moves toward the basal end side and the moving body 57 and the slider 44 move toward the basal end sides. In consequence of this motion of the slider 44, the pin 46 presses the inner wall surface of the basal end side of the oblong hole 43 and the movable nipping piece 42 revolves round the pin 45 as the center and closes (the state shown in FIG. 10).

The open-close motion of the movable nipping piece 42 is synchronized with the rotation of the knob 921 and the opening degree between the stationary nipping piece 41 and the movable nipping piece 42 (grasping force) is proportioned to the amount of the rotation of the knob 921. By adjusting the amount of the rotation of the knob 921, therefore, the opening degree between the stationary nipping piece 41 and the movable nipping piece 42 can be freely set. The transmitting member 6 is supported by the supporting part 54 of the locking means 7B. When the hand is removed from the knob 921, therefore, the existing opening degree between the stationary nipping piece 41 and the movable nipping piece 42 is retained and fixed.

Particularly when the transmitting member 6 has the tension thereof varied by a bend or a curve produced in the main body 2 of the instrument as when the instrument is provided with the curving part 23 formed of the aforementioned joint rings 24 illustrated in FIG. 7, the posture of the surgically operating means 4 or the opening degree of the movable nipping piece 42 is not varied because the rotary shaft 51, the moving body 57 and the slider 44 are not moved.

Incidentally, the open-close motion of the surgically operating means 4 is obtained invariably when the main body 2 of the instrument is in a straight state and when it is in a bent or curved state.

Figure 11:
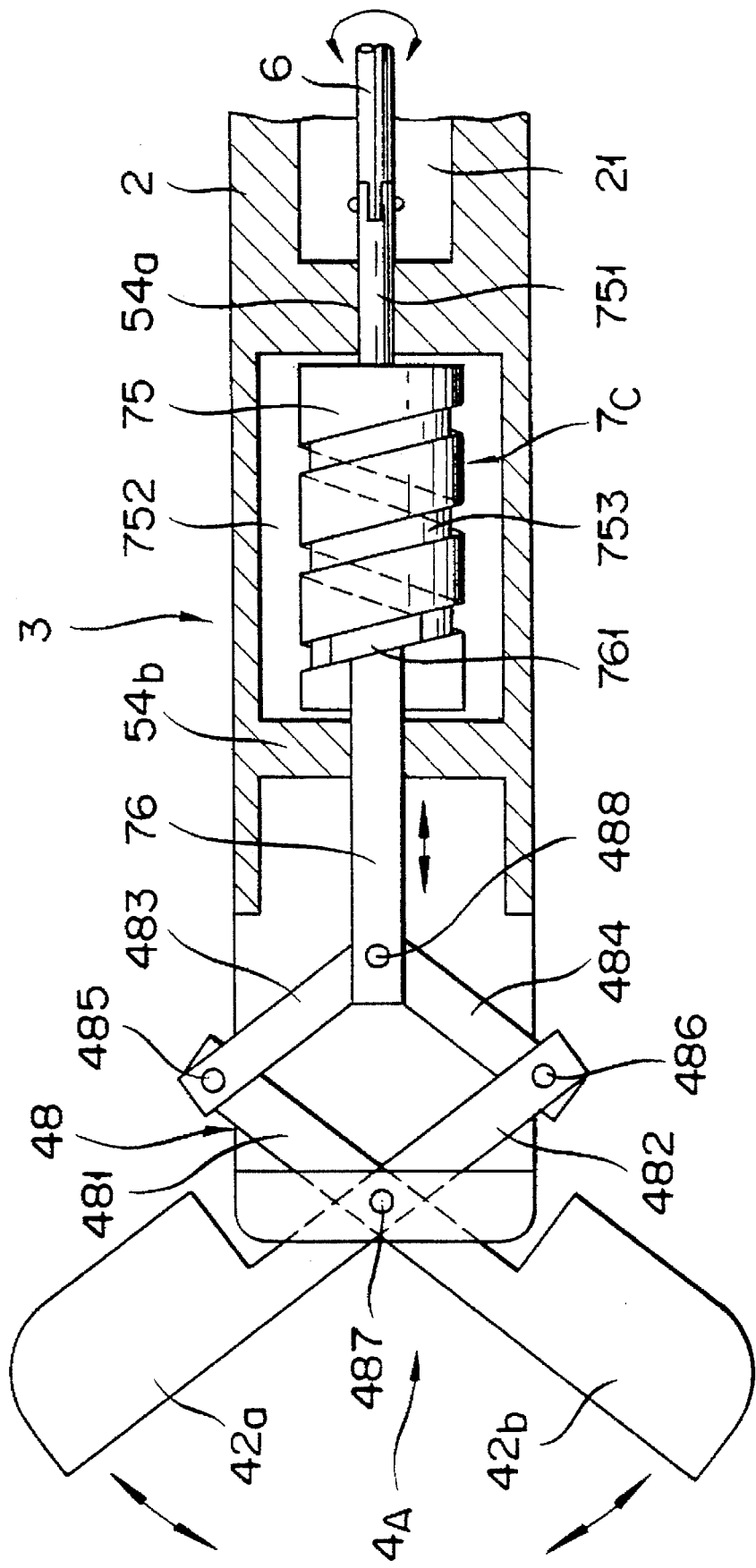
FIG. 11 is a partially sectioned side view illustrating another example of the construction of surgically operating means and converting means of the second embodiment.

FIG. 11 is a partially sectioned side view illustrating another example of the construction of the surgically operating means and the locking means in the second embodiment.

A surgically operating means 4A, as shown in the diagram, constitutes itself the mechanism of a forceps which is capable of nipping vital tissue. It is provided with a pair of movable nipping pieces 42a and 42b which are revolved round a pin 487 disposed in the leading end part of a main body 2 of the instrument.

An extending part 481 is formed on the basal end side of the movable nipping piece 42b past the pin 487. The basal end part of the extending part 481 is revolvably supported on the leading end part of a link 483 with a pin 485. An extending part 482 is formed on the basal end side of the other movable nipping piece 42a past the pin 487. The basal end part of this extending part 482 is revolvably supported on the leading end part of a link 484 with a pin 486. The basal end parts of the links 483 and 484 are revolvably supported on the leading end part of a following member 76 which will be specifically mentioned hereinbelow with a pin 488.

The extending parts 481 and 482, the links 483 and 484, and the pins 485, 486, 487, and 488 jointly form a link mechanism 48 which converts a linear motion of the following member 76 into rotary motions of the movable nipping pieces 42a and 42b.

A locking means 7C is composed of a tubular cam (rotary body) 75, the following member (counter body) 76 adapted to move in the longitudinal direction by following the rotation of the cam 75, a supporting part 54a for rotatably supporting a rotary shaft 751 of the cam 75, and a supporting part 54b for supporting the following member 76 movably in the longitudinal directions thereof and an accommodating space 752 of the cam 75.

The cam 75 is so disposed that it may be rotatable within the accommodating space 752 but may not be movable at all in the direction of the rotary axis or may be movable over only a small distance such that the motion will cause no substantial change in the posture of the surgically operating means 4A.

The basal end of the rotary shaft 751 of the cam 75 is connected to the leading end of the transmitting member 6.

On the periphery of the cam 75 is formed a spiral cam groove 753. A projecting part 761 is formed on the basal end of the following member 76. This projecting Wart 761 is inserted in the cam groove 753. Optionally, the supporting part 54b may be provided with a bearing (not shown).

When the knob 921 is rotated in a stated direction, the transmitting member 6, the rotary shaft 751 and the cam 75 are rotated in the same manner as described above. As a result, the projecting part 761 is moved along the cam groove 753 and the following member 76 is moved in the direction of the rotary axis of the cam 75 and, owing to the action of the link mechanism 48 mentioned above, the movable nipping pieces 42a and 42b of the surgically operating means 4A are opened and closed.

The locking means 7C substantially inhibits the motion of the transmitting member 6 in the longitudinal direction thereof by causing the motion of the cam 75 in the direction of the rotary axis by means of the supporting parts 54a and 54b, with the result that the posture of the surgically operating means 4A or the opening angle of the movable nipping pieces 42a and 42b will be fixed.

Figure 12:
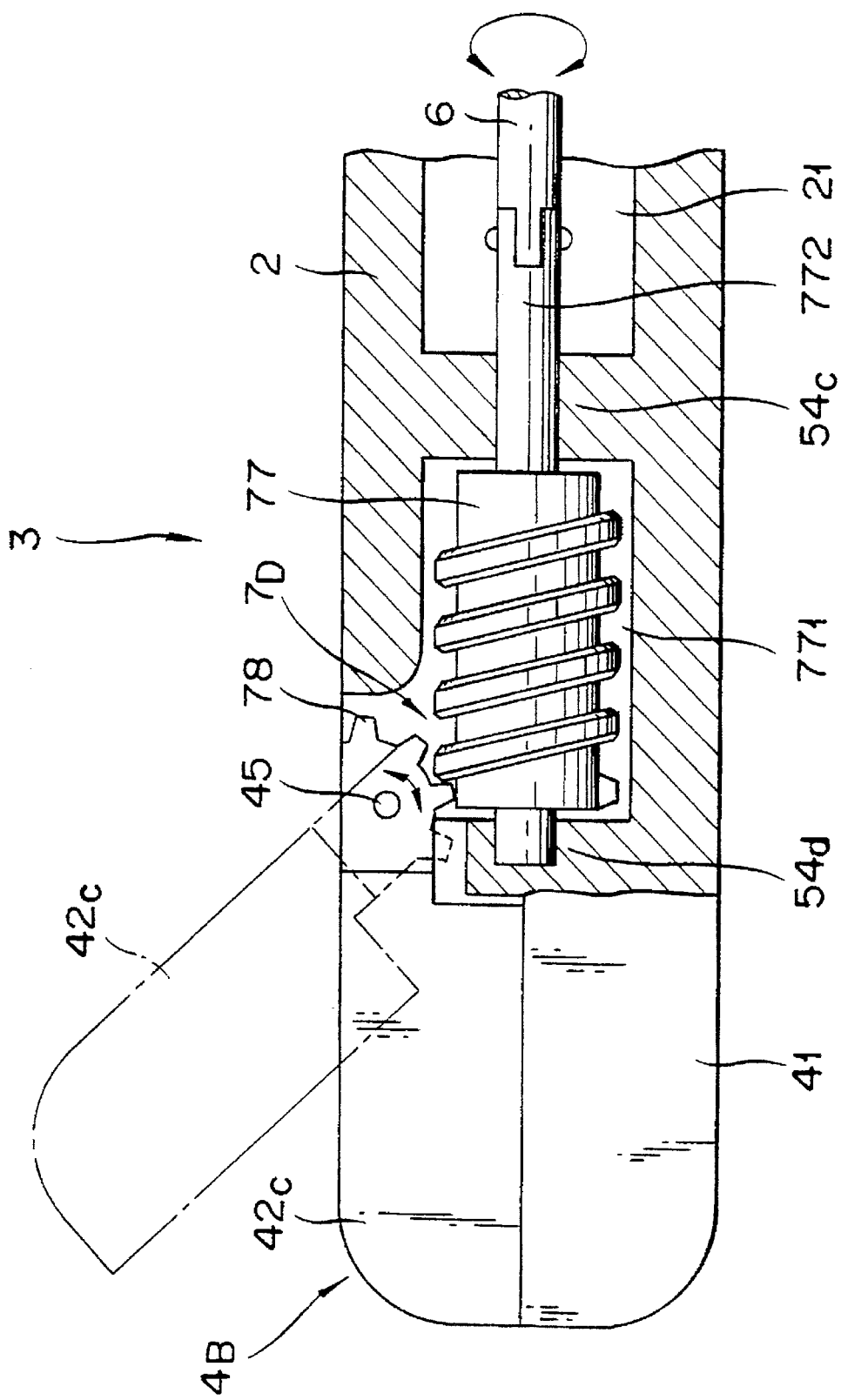
FIG. 12 is a partially sectioned side view illustrating yet another example of the construction of surgically operating means and converting means of the second embodiment.

FIG. 12 is a partially sectioned side view illustrating yet another example of the construction of the surgically operating means and the locking means in the second embodiment.

A surgically operating means 4B, as shown in the diagram, is provided with a stationary nipping piece 41 and a movable nipping piece 42c adapted to revolve relative to the stationary nipping piece 41. The movable nipping piece 42c is revolvably disposed in the leading end part of the main body 2 of the instrument with a pin 45.

A locking means 7D is composed of a worm (rotary body) 77, a worm gear (counter body) 78 connected or joint to the basal end of the movable nipping piece 42c and meshed with the worm 77, an accommodating space 771 for the worm 77 formed in the leading end part of the main body 2 of the instrument, and supporting parts 54c and 54d for rotatably supporting a rotary shaft 772 of the worm 77.

The worm 77 is so disposed that it may be rotatable within the accommodating space 771 but may not be movable at all in the direction of the rotary axis or may be movable over only a small distance such that the motion will cause no substantial change in the posture of the surgically operating means 4B.

The basal end of the rotary shaft 772 of the worm 77 is connected to the leading end of the transmitting member 6. The worm gear 78 rotates round the pin 45 as the center. Optionally, the supporting parts 54c and 54d may be each provided with a bearing (not shown).

When the knob 921 is rotated in a stated direction in the same way as stated above, the transmitting member 6, the rotary shaft 772 and the worm 77 are rotated. As a result, the worm gear 78 rotates round the pin 45 as the center and the movable nipping piece 42c is opened and closed.

The locking means 7D substantially inhibits the motion of the transmitting member 6 in the longitudinal direction thereof by causing the motion of the worm 77 in the direction of the rotary axis by means of the supporting parts 54c and 54d, with the result that the posture of the surgically operating means 4B or the opening angle of the movable nipping piece 42c will be fixed.

In the construction shown in FIG. 12, the movable nipping piece 42c is directly rotated by the rotation of a worm gear 78. The construction of the locking means 7D is not limited to what is shown in the diagram. Instead, a construction which causes the slider 44 to be moved in the same manner as described above by the rotation of the worm 77, a construction which comprises a pinion gear rotated by the rotation of the transmitting member 6 and a rack gear meshed with the pinion gear, a construction which comprises at least one pair of mutually meshed bevel gears, or a construction which combines any of the constructions mentioned above with the aforementioned link mechanism may be adopted on the condition that the conversion of the rotation of the transmitting member 6 into an open-close motion or a rotary motion of the surgically operating means 4B be accomplished thereby.

In the examples of the construction shown in FIG. 11 and FIG. 12, the same urging means as described above may be incorporated for the purpose of relieving the rotary body and the counter body of backlash.

Incidentally, the locking means 7B, 7C, 7D constructed as illustrated may be disposed inside the main body 2 of the instrument and near the leading end part 3 (on the leading end side of the curving part 23 when the main body 2 of the instrument is adapted to produce a bend or a curve).

Figure 13A:
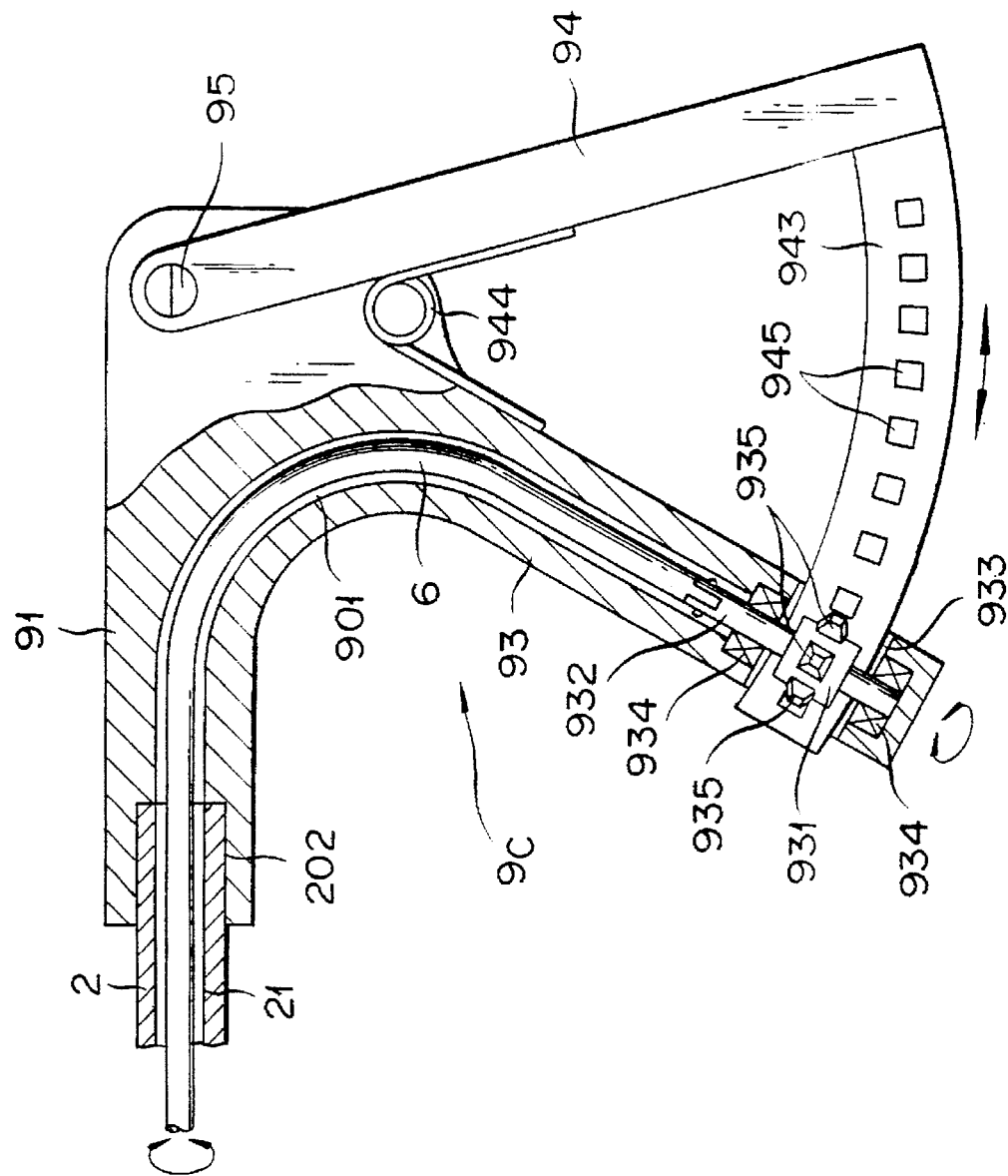
FIG. 13A is a partially sectioned side view illustrating another example of the construction of a manipulating part of the second embodiment.

FIG. 13A is a partially sectioned side view showing another example of the construction of the manipulating part. A manipulating part 9C shown in the diagram is composed of a stationary handle 93 fixed relative to a main body 91 of the manipulating part or disposed integrally therewith, a movable handle 94 adapted to be opened or closed (revolved) relative to the stationary handle 93, a rotor-driving member 943 which is an arcuate plate disposed in the end part of the movable handle 94 on the opposite side from the center of revolution thereof, a rotor 931 connected to the basal end part of the transmitting member 6, and an urging member 944 for urging the movable handle 94 in the direction of increasing the opening angle between the movable handle 94 and the stationary handle 93.

A basal end part 202 of the main body 2 of the instrument is set in the leading end part of the main body 91 of the manipulating part. From this part along the interior of the stationary handle 93 through the lower end part of the stationary handle 93 in FIG. 13A, a curved passage 901 which communicates with an empty space 21 of the main body 2 of the instrument is formed. The transmitting member 6 is inserted into the passage 901.

In the lower end part in FIG. 13A of the stationary handle 93, a guide groove 933 piercing the stationary handle 93 is formed. Inside this guide groove 933, the rotor 931 is rotatably disposed. Specifically, the opposite ends of a rotary shaft 932 of the rotor 931 are supported by a pair of bearings 934. On the outer circumferential surface of the rotor 931, a plurality of protuberances (sprockets) 935 for insertion into (engagement with) openings 945 which will be specifically mentioned hereinbelow are protrudingly formed as arranged in a radial pattern.

The movable handle 94 in the upper end part thereof in FIG. 13A is attached rotatably to the main body 91 of the manipulating part with a shaft member 95. To the lower end in FIG. 13A of the movable handle 94, the basal end of the rotor-driving member 943 centering around the shaft member 95 is attached or joined. In this rotor-driving member 943, a plurality of openings 945 are formed desirably as regularly spaced along the longitudinal direction of the member 943. The leading end part of the rotor-driving member 943 is inserted through the neighborhood of the bottom inside the guide groove 933 and the openings 945 and protuberances 935 are meshed.

An urging member 944 formed of a torsion spring is interposed between the stationary handle 93 and the movable handle 94. By this urging member 944, the movable handle 94 is urged in the direction of increasing the opening angle of the stationary handle 93.

When the movable handle 94 so held as to assume the state shown in FIG. 13A is rotated clockwise in FIG. 13A with the stationary handle 93 and the movable handle 94 gripped in a hand, the rotor-driving member 943 inside the guide groove 933 is moved in the longitudinal direction thereof and, by virtue of the engagement of the openings 945 with the sprockets 935, the rotor 931 is rotated. As a result, the transmitting member 6 is rotated and the leading end part 3 thereof is actuated desirably so as to close the surgically operating means 4, 4A, or 4B through the locking means 7A, 7B, or 7C as described above.

When the grip of a hand on the two handles 93 and 94 is either eliminated or relaxed, the urging force of the urging member 944 revolves the movable handle 94 counterclockwise in FIG. 13A and the rotor 931 is rotated in the direction opposite to the direction mentioned above. As a result, the transmitting member 6 rotates in the direction opposite to the direction mentioned above and the leading end part 3 thereof is actuated desirably to open the surgically operating means 4, 4A, or 4B.

The manipulating part 9C constructed as described above excels in the efficiency of operation as evinced by the fact that it can be operated with one hand gripping the stationary handle 93 and the movable handle 94.

Figure 13B:
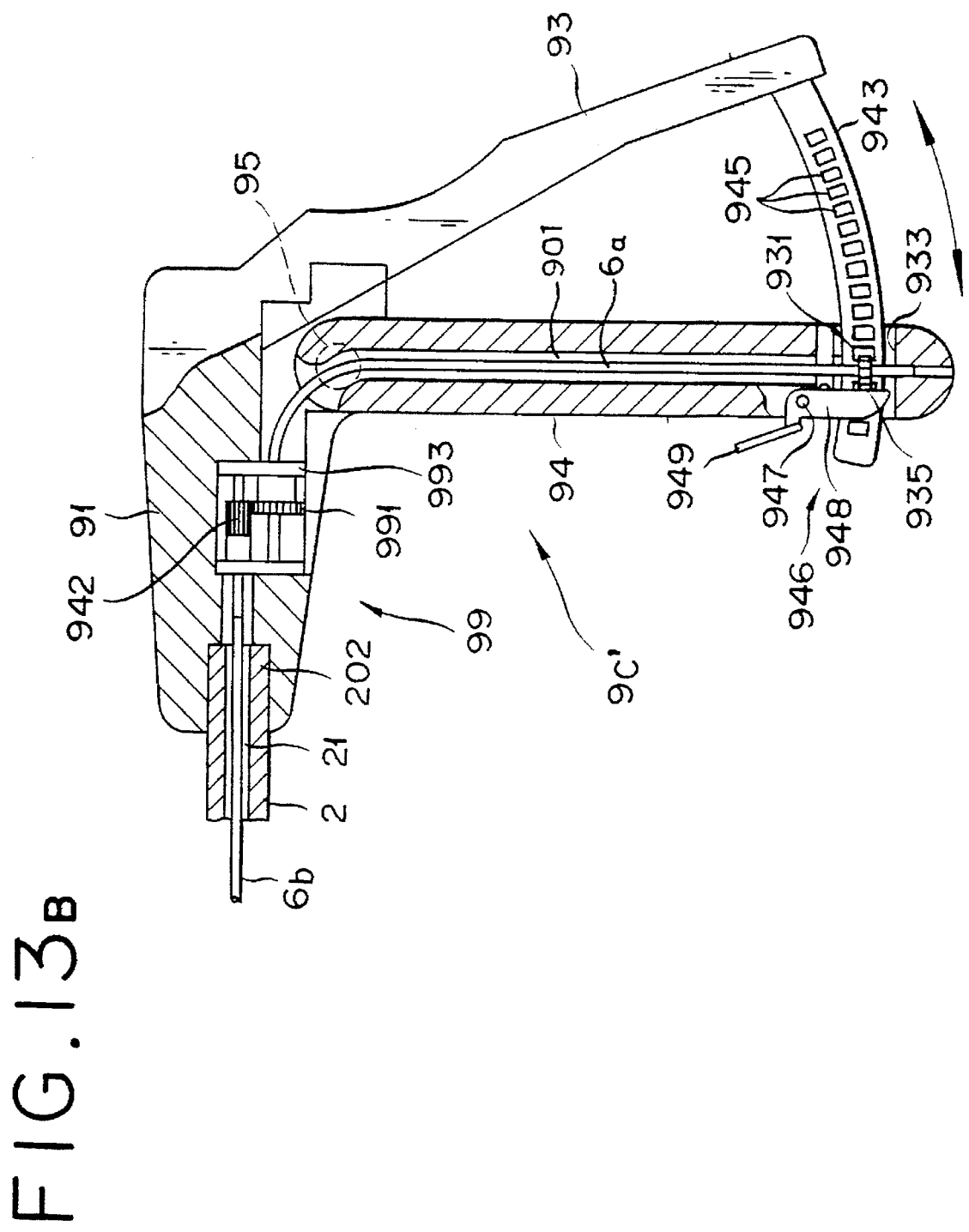
FIG. 13B is a partially sectioned side view illustrating yet another example of the construction of the manipulating part of the second embodiment.

FIG. 13B is a partially sectioned side view showing yet another example of the construction of the manipulating part. In this example of the construction, the stationary handle 93 and the movable handle 94 have reversed positions from those used in the example of FIG. 13A.

A manipulating part 9C' shown in FIG. 13B is provided with a stationary handle 93 fixed on or joined integrally to a main body 91 of the manipulating part, a movable handle 94 adapted to be opened or closed (revolved) relative to the stationary handle 93, a rotor-driving member 943 disposed in the end part of the stationary handle 93, a rotor 931 connected to the end part of a transmitting member 6a disposed inside a passage 901 in the movable handle 94, and a gear mechanism 99 for transmitting the rotation of the rotor 931 to a transmitting member 6b disposed inside the empty space 21 of the main body 2 of the instrument.

The movable handle 94 in the upper end part in FIG. 13B comprises a shaft member 95 which projects from the opposite sides of the movable handle 94 and is rotatably attached with the half-divided main body 91 of the manipulating part. In the lower end of the movable handle 94 in FIG. 13B, a guide groove 933 piercing the movable handle 94 is formed. Inside the guide groove 933, the rotor 931 is revolvably disposed. On the outer circumferential surface of the rotor 931, a plurality of protuberances (sprockets) 935 for insertion into (engagement with) openings 945 of the rotor-driving member 943 are protrudingly formed as arranged in a radial pattern. This rotor 931 is adapted to be stopped by a stopping mechanism 946. This stopping mechanism 946 is provided with a stopping piece 948 adapted to swing round a pin 947 as the center. The revolution of the rotor 931 is stopped by manipulating a protruding piece 949 thereby causing the stopping piece 948 to engage the protuberance 935 formed on the outer circumferential surface of the rotor 931. To the lower end of the stationary handle 93 in FIG. 13B, the basal end of the rotor-driving member 943 which centers round the shaft member 95 is fixed or integrally joined. In this rotor-driving member 943, a plurality of openings 945 are formed along the longitudinal direction desirably as regularly spaced. The leading end part of the rotor-driving member 943 is passed through the neighborhood of the bottom part of the guide groove 933 to establish engagement between the openings 945 and the protuberances 935.

The present construction, like the construction shown in FIG. 13A, may be provided between the stationary handle 93 and the movable handle 94 with an urging member 944 adapted to urge the movable handle 94 in the direction of increasing the opening angle of the movable handle 94 relative to the stationary handle 93.

The gear mechanism 99 is provided with a first gear 991 to which the end part of the transmitting member 6a in the movable handle 94 is connected and a second gear 992 to which the end part of the transmitting member 6b in the main body 2 of the instrument. These gears 991 and 992 are rotatably supported in a case 993 as held in a mutually meshed state and are utilized for transmitting the revolution of the rotor 931 from the transmitting member 6a to the transmitting member 6b.

When the movable handle 94 so held as to assume the state shown in FIG. 13B is rotated counterclockwise in the FIG. 13B with the stationary handle 93 and the movable handle 94 gripped in a hand, the movable handle 94 is moved along the rotor-driving member 943 as guided by the guide groove 933 and, by virtue of the engagement of the openings 945 with the protuberances 935, the rotor 931 is rotated. As a result, the transmitting member 8a is rotated. This rotation is transmitted via the gear mechanism 99 to the transmitting member 6b.

Then, at the leading end part 3, the surgically operating means 4, 4A, or 4B is actuated so as to be desirably closed through the locking means 7A, 7B, or 7C as described above.

When the movable handle 94 is manually revolved clockwise in FIG. 13B or it is revolved clockwise by the urging force of the urging member interposed between the two handles 93 and 94, the rotor 931 is rotated in the direction opposite to the direction mentioned above. The transmitting member 6, consequently, is rotated in the direction opposite to the direction mentioned above and the leading end part 3 is actuated desirably so as to open the surgically operating means 4, 4A, or 4B.

The manipulating part 9C' constructed as described above is at an advantage in not merely enabling the stationary handle 93 and the movable handle 94 to be manipulated in one hand but also further enhancing the operational efficiency as evinced by the fact that the movable handle 94 is actuated as though it were being drawn toward the stationary handle 93.

Incidentally, in the manipulating part 9C or 9C', the movable handle 94 may be adapted to produce a parallel translation relative to the stationary handle 93. It is also permissible to have a desired mechanism interposed between the movable handle 94 and the rotor-driving member 943 or the movable handle 94 and the stationary handle 93. Further, the engagement between the rotor-driving member 943 and the rotor 931 does not need to be limited to the construction illustrated in the diagram. An engagement between a rack gear and a pinion gear adapted to be meshed with the rack gear, an engagement between a pressing surface and a roller adapted to be pressed against the pressing surface, or an engagement between a cord and a reel adapted to take up the cord may be adopted instead, for example.

Instead of providing the manipulating part 9C with the urging member 944, such an urging member as a spring (not shown) which urges the transmitting member 6 into rotation in a prescribed direction may be provided near the leading end part 3. It is also permissible to omit completely the provision of any of such urging members as have been described above.

In the example of FIG. 13B the transmitting member may be composed of a single member integrated with not only the transmitting members 6a and 6b connected together through the gear mechanism 99 but a part disposed from the rotor 931 similar to in FIG. 13A to the leading end part 3.

As shown in FIGS. 13A and 13B, in the examples according to the invention the transmitting member 6, the rotor and the rotor-driving member may be disposed in the stationary handle or the movable handle optionally. Furthermore, the stationary handle may be disposed before and behind the movable handle. In consequence, it is understood that the movable handle and the stationary handle and/or the transmitting member, the rotor and the rotor-driving member may be arranged variously. For example, in case of disposing one of the rotor and the rotor-driving member in the movable handle, the other of the rotor and the rotor-driving member does not absolutely require to be disposed in the stationary handle though the rotor is provided in one of the movable handle and the stationary handle and the rotor-driving member is provided in the other of the movable handle and the stationary handle as shown in the diagram. Namely, the other of the rotor and the rotor-driving member may be disposed in a raised portion formed in the stationary handle.

Also in the present embodiment, the curving part 23 of the main body 2 of the instrument may be formed of such a plurality of joint rings 24 as shown in FIG. 7.

In the embodiments cited above, the surgically operating means 4, 4A, and 4B are made to fix their posture by preventing the transmitting member 6 from moving in the longitudinal direction by the locking means 7A through 7D. Optionally, the leading end part 3 may be rotatable relative to the main body 2 of the instrument (FIGS. 14 through 19).

In the surgical instruments shown in FIGS. 14 through 19, like component parts found in those cited above are denoted by like reference numerals. The description of these component parts are partially omitted below.

Figure 14:
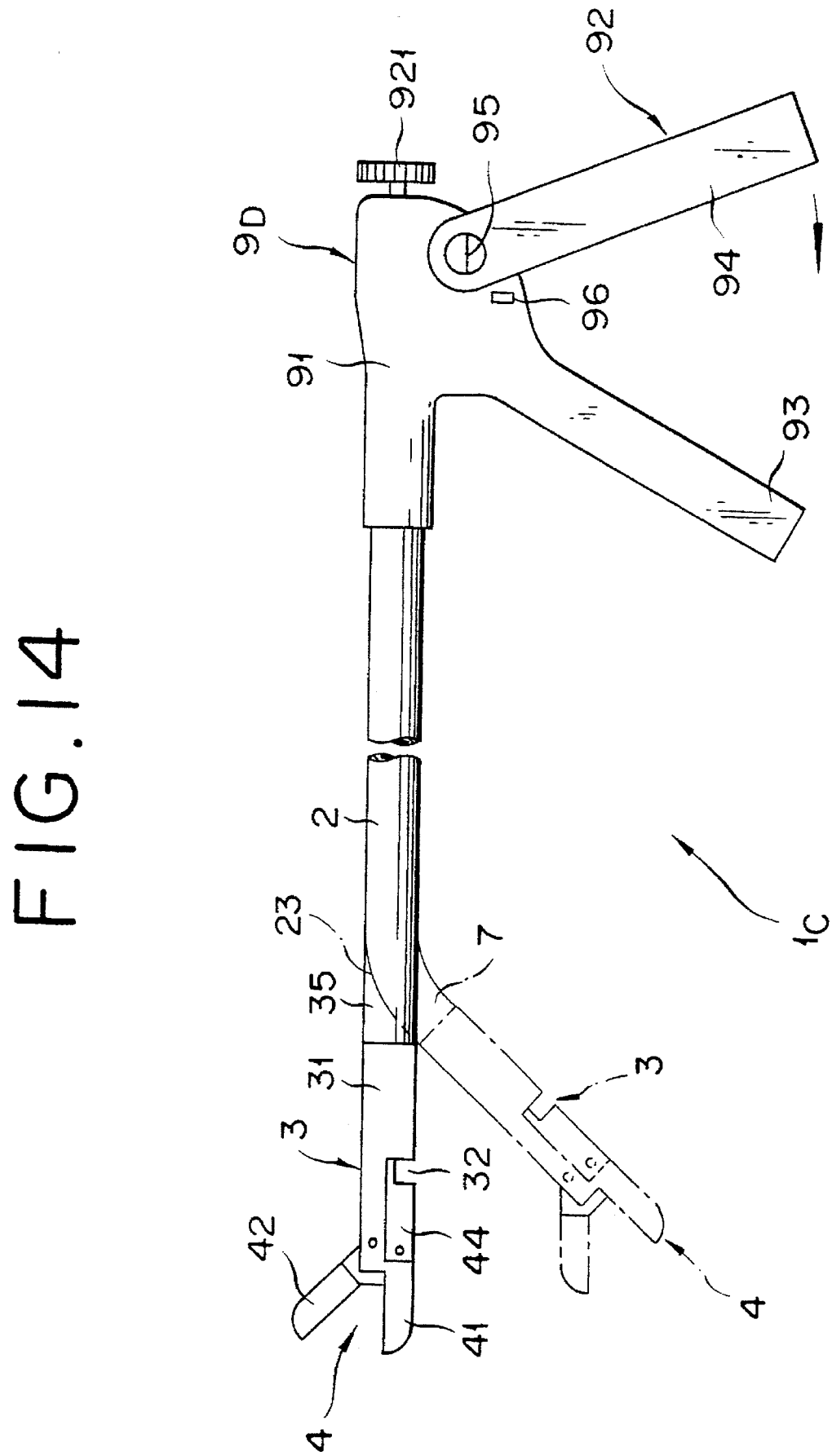
FIG. 14 is an overall side view illustrating a modified example of the surgical instrument according to this invention.
Figure 15:
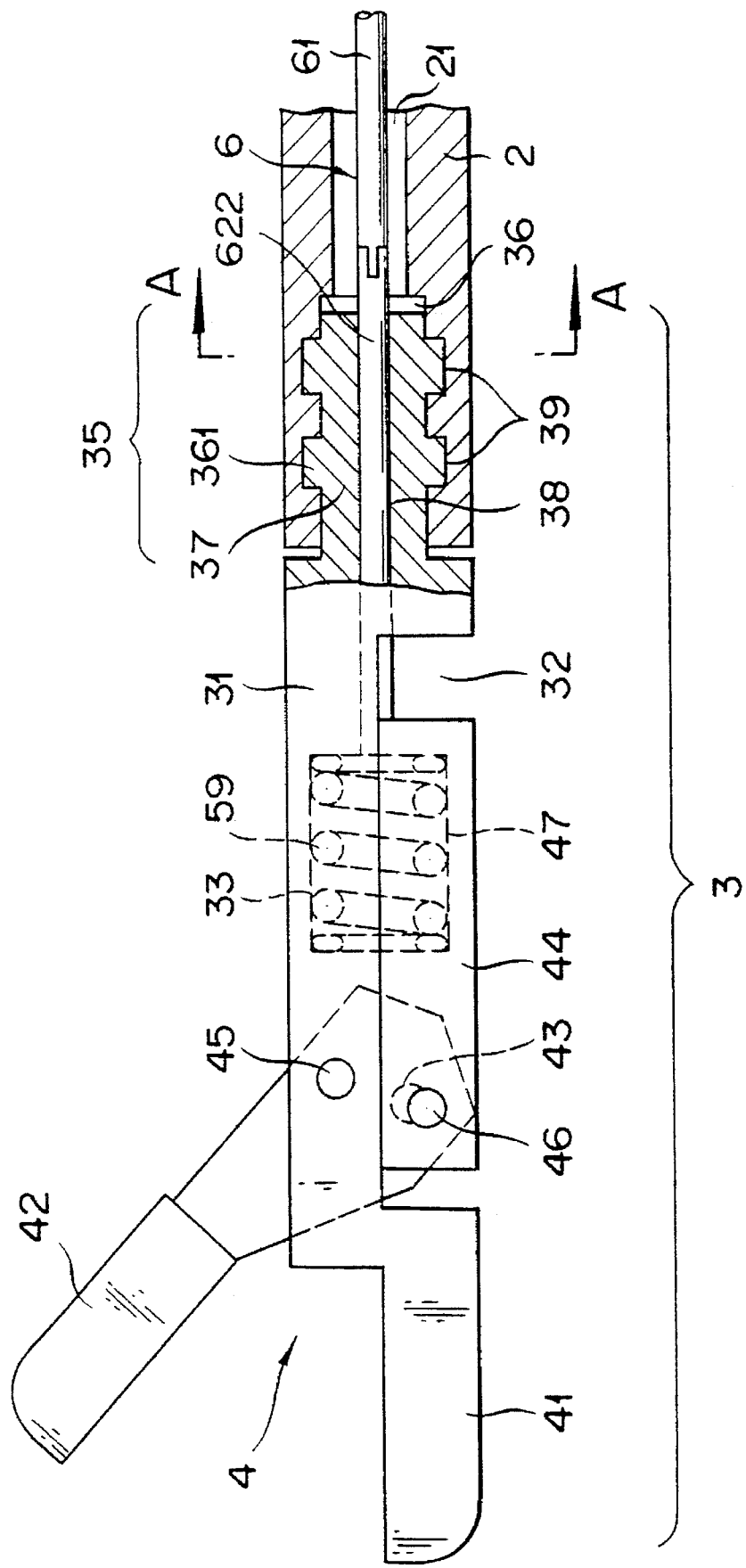
FIG. 15 is a partially sectioned side view illustrating as magnified the construction near the leading end part of the surgical instrument shown in FIG. 14.
Figure 16:
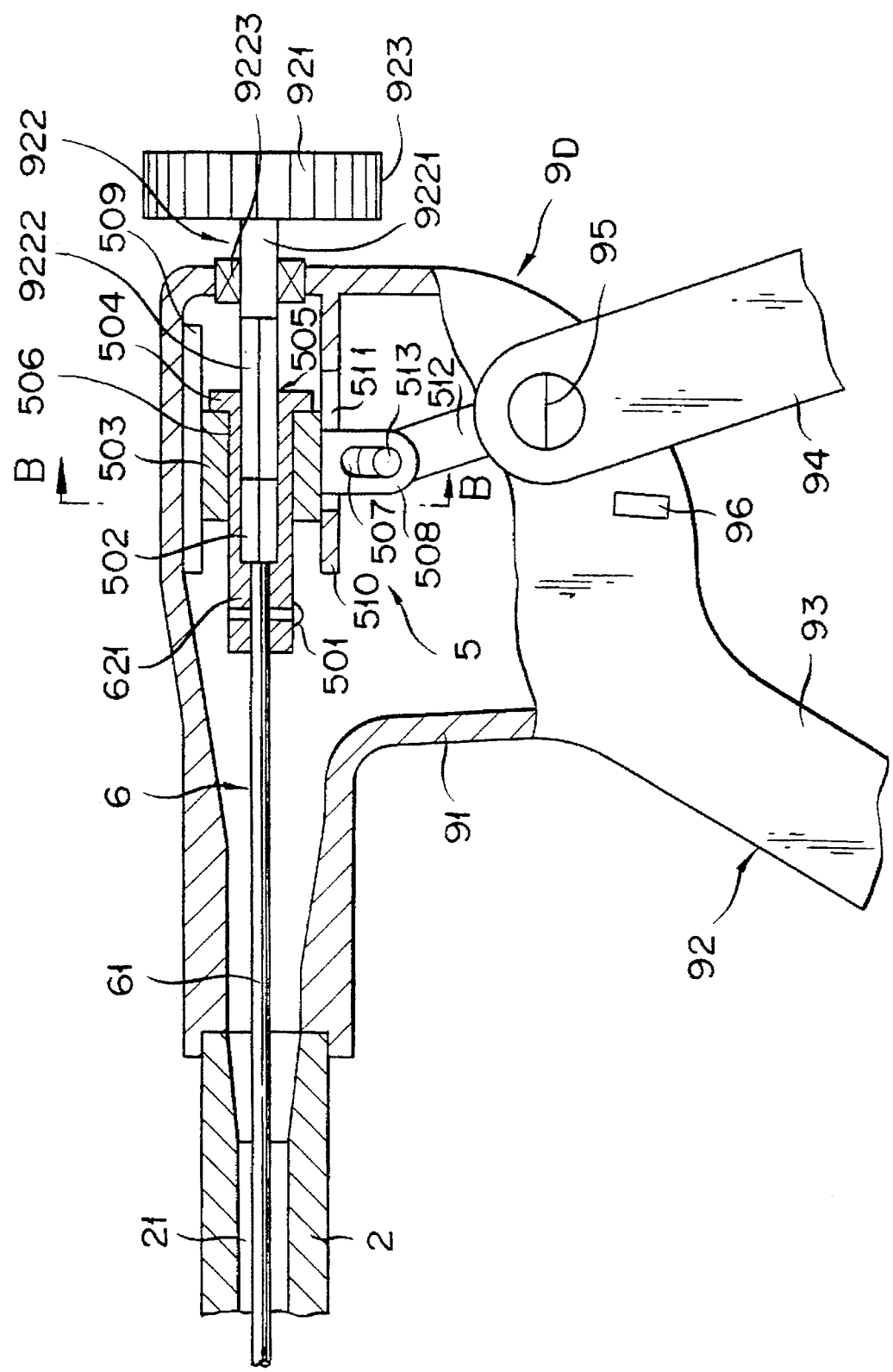
FIG. 16 is a partially sectioned side view illustrating as magnified the construction near the basal end part of the surgical instrument shown in FIG. 14.

A surgical instrument (forceps) 1C shown in FIGS. 14 through 16 is provided with an elongate main body 2 of the instrument, a leading end part 3 disposed on the leading end side of the main body 2 of the instrument and furnished with a surgically operating means 4 for producing an open-close motion or a rotary motion, a manipulating part 9D disposed on the basal end side of the main body 2 of the instrument, and an elongate transmitting member 6 interconnecting the leading end part 3 and the manipulating part 9D.

The main body 2 of the instrument, as shown in FIG. 15, is a hollow elongate member having formed therein an empty space 21 capable of accommodating the transmitting member 6. It is provided at the leading end thereof with a joining part 35 which is rotatably connected to the leading end part 3.

The transmitting member 6 is composed of a linear body 61, a first connecting member 621 connected to the basal end side of the linear body 61, and a second connecting member 622 connected to the leading end side of the linear body 61. The linear body and the connecting members 621 and 622 are identical in materials, outside diameters, etc. with those already mentioned.

Figure 17:
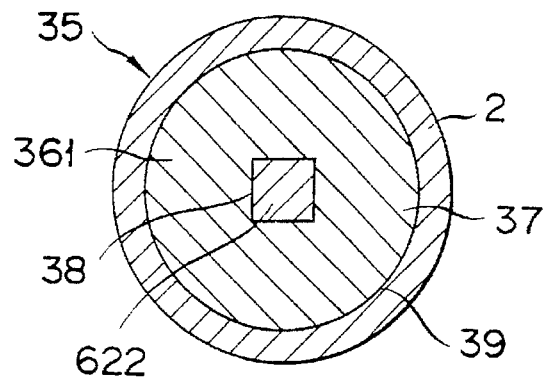
FIG. 17 is a cross section taken through FIG. 15 along the line A—A.

The second connecting member 622, as shown in FIG. 17, has a square lateral cross-section. In the central part of a protuberance 37 in a connecting part 35 which will be specifically mentioned hereinbelow, a passage 38 of a similar shape is formed. The second connecting member 622 is inserted in the passage 38 and allowed to slide along the inner wall of the passage 38. Then, the leading end of the second connecting member 622 is made to reach the interior of the leading end part 3 and connected or joined integrally to the basal end of a slider 44 which will be specifically mentioned hereinbelow.

Incidentally, the shape of the lateral cross section of the second connecting member 622 is not limited to that which is shown in FIG. 17. The cross section may be in any desired shape on the condition that it be capable of obstructing the rotation of the member 622 relative to the passage 38. As concrete examples of the cross section, a triangle, a hexagon, a semi-circle, a bar, a cross, and the shape of the letter L may be cited.

A notch 32 is formed in the lower part of the main body 31 of the leading end part in FIG. 15. Inside this notch 32 is disposed a slider 44 which is capable of sliding in the longitudinal direction of the leading end part 3. A pin 46 is projected from the leading end part of the slider 44. This pin 46 is inserted in an oblong hole 43 which is formed in the lower part of the basal end of a movable nipping piece 42.

Owing to the construction described above, the transmitting member 6 is drawn toward the basal end side by the manipulation of a handle part 92 which will be specifically mentioned hereinbelow. The stationary nipping piece 41 and the movable nipping piece 42 are in a closed state when the slider 44 is positioned on the basal end side in the notch. The pin 46 is pressed against the inner wall surface of the oblong hole 43, the movable nipping piece 42 is rotated round the pin 45 as the center, and the movable nipping piece 42 is opened (in the state shown in FIG. 15) when the transmitting member 6 is moved toward the leading end side and the slider 44 is moved toward the leading end side in the notch 32 in consequence of relaxation or elimination of the grasping force exerted on the handle part 92 which will be specifically mentioned hereinbelow.

A coil spring 59 is accommodated in a compressed state in a recess 33 formed in the main body 31 of the leading end part and in a recess 47 formed in the slider 44. This coil spring 59 is urging means which by the elastic force thereof urges the slider 44 toward the leading end, namely in the direction of opening the movable nipping piece 42. Since the present embodiment has the coil spring 59 as urging means built in the leading end part 3 as described above, it simplifies the construction of the manipulating part 9B and improves the efficiency of operation thereof because the construction, unlike the conventional forceps, does not require the handle part 92 to be provided with a leaf spring or other means for urging the movable handle 94 in the direction of opening it.

A connecting part 35, as shown in FIG. 15, is composed of a recess 36 having a circular lateral cross section so formed as to communicate with the empty space 21 of the main body 2 of the instrument and open in the leading end surface of the main body 2 of the instrument and a protuberance 37 of a circular lateral cross section projected from the basal end of the main body 31 of the leading end part and intended to be inserted in the recess 36 mentioned above. In the central part of the protuberance 37, a passage 38 substantially identical in lateral cross section with the second connecting member 622 is formed in the axial direction. The second connecting member 622 is inserted in this passage 38 to effect transmission of the rotating force of the transmitting member 6 to the protuberance 37 and the main body 31 of the leading end part.

On the inner wall surface of the recess 36, two annular grooves 39 are formed as separated with a stated interval in the axial direction. On the outer wall surface of the protuberance 37, two annular raised portions 361 are formed along the circumferential direction at the positions corresponding to the grooves 39. These raised portions 361 are inserted into the corresponding grooves 39. Incidentally, the raised portions 361 do not need to be limited to the shape of a complete ring but may be formed of segments arranged intermittently in a circle.

By the connecting part 35 constructed as described above, the leading end part 3 is allowed to rotate relative to the main body 2 of the instrument and inhibited from producing a notable motion in the axial direction. As a result, the leading end part is prevented from falling off or producing backlash.

Incidentally, the leading end part 3 may be provided with means (not shown) which is capable of abating the resistance offered to the rotation thereof. As concrete examples of this means, the interposition of a lubricating agent such as lubricating oil between the recess 36 and the protuberance 37 and the formation of a layer of such low-friction material as polytetrafluoroethylene, silicone, polyethylene, polyacetal, or brass therebetween may be cited. By this means, the rotation of the leading end part 3 can be smoothed.

On the basal end side of the main body 2 of the instrument, a manipulating part 9D for remotely producing an open-close motion of the surgically operating means 4 is disposed as shown in FIG. 14 and FIG. 16. This manipulating part 9D is provided with a handle part 92 composed of a stationary handle 93 fixed or integrally joined to the main body 91 of the manipulating part and a movable handle 94 adapted to be opened or closed (revolved) relative to the stationary handle 93.

The movable handle 94 in the upper end part thereof in the diagram is attached revolvably to the main body 91 of the manipulating part by means of a shaft member 95.

Then, from the outer surface of the lower part of the main body 91 of the manipulating part, a stopper 96 adapted to be engaged with the movable handle 94 and consequently enabled to regulate the range of the revolution thereof is projectingly formed. By this arrangement, the otherwise possible breakage of the transmitting member 6 due to the exertion of unduly large grasping force on the handle part 92 can be prevented. The position of the stationary handle 93 and the movable handle 94 may be reversed.

The manipulating part 9D is further provided on the basal end side of the main body 91 thereof with a knob 921. A rotary shaft 922 of the knob 921 forms a cylindrical part 9221 on the basal end side and an angular column part 9222 on the leading end side. The cylindrical part 9221 is supported by a bearing 9223. On the periphery of the knob 921, irregularities 923 are formed along the axial direction of the knob 921.

Inside the main body 91 of the manipulating part is disposed converting means 5 which converts the rotation of the movable handle 94 into a motion of the transmitting member 6 in the longitudinal direction and, at the same time, transmits turning force generated by the rotation of the knob 921 to the transmitting member 6.

Figure 18:
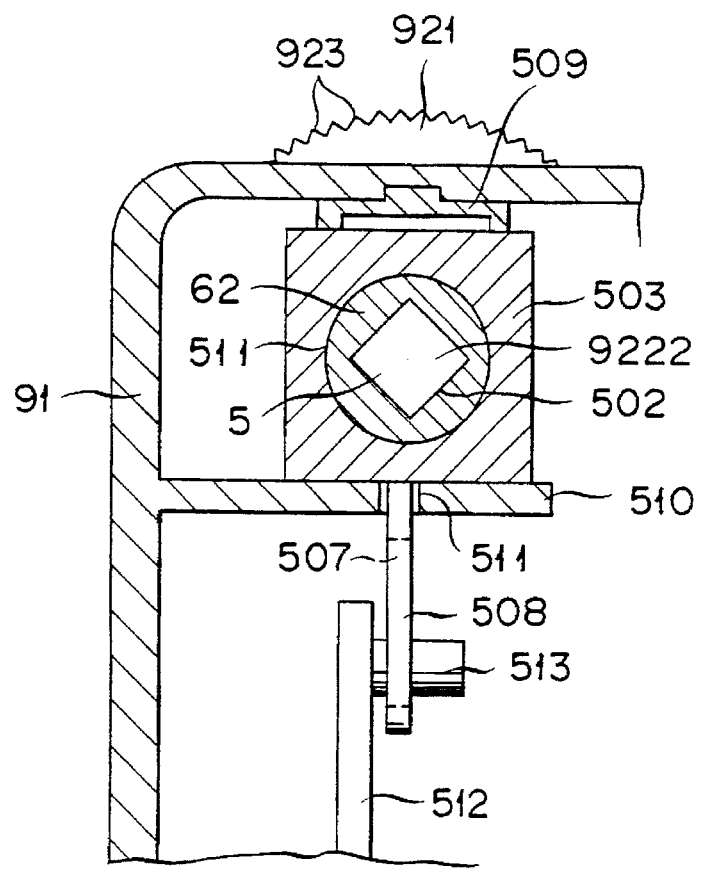
FIG. 18 is a cross section taken through FIG. 16 along the line B—B.

This converting means 5, as shown in FIG. 16 and FIG. 18, is fixed to the leading end part of a first connecting member 621 by means of a pin 501. This first connecting member 621 is a cylindrical member which has formed in the central part thereof a passage 502 of a square cross section permitting insertion therein of the angular column part 9222 of the rotary shaft 922 of the knob 921. At the basal end of the first connecting member 621 is formed a rib 504 for engagement with the basal end surface of the supporting member 503 which will be specifically mentioned hereinbelow.

The converting means 5 is provided with the supporting member 503 for rotatably supporting the first connecting member 621 and a turning force-transmitting mechanism 505 for transmitting the turning force of the knob 921 to the first connecting member 621.

The supporting member 503 is provided with a through hole 506 of a circular lateral cross section for permitting insertion therein of the first connecting member 621. In the lower part of the supporting member 503 in the diagram, a tongue piece 508 having an elongate hole 507 formed therein is projectingly formed. The supporting member 503 is supported by guide members 509 and 510 formed inside the main body 91 of the manipulating part so as to be slidably supported in the longitudinal direction of the transmitting member 6. The tongue piece 508 pierces a slit 511 formed in the lower guide member 510 and protrudes downward from the slit 511.

On the movable handle 94 is formed a projecting piece 512 which is inserted into the main body 91 of the manipulating part. A pin 513 raised from the upper end part of the projecting piece 512 is inserted in the elongate hole 507 of the tongue piece 508.

The turning force-transmitting mechanism 505 is composed of the angular column part 9222 mentioned above and the passage 502 for permitting insertion therein of the angular column part 9222. The angular column part 9222 can be axially moved relative to the passage 502 but cannot be rotated relative to the passage 502 without reference to the depth of insertion thereof into the passage 502. As a result, the turning force of the knob 921 is transmitted to the first connecting member 621 through the angular column part 9222 and the passage 502 and enabled to impart rotation to the transmitting member 6 as a whole.

Incidentally, the shape of the lateral cross section of the angular column part 9222 is not limited to that which is shown in the diagram. The cross section may be in any desired shape on the condition that it be capable of obstructing the rotation of the angular column part 9222 relative to the passage 502. As concrete examples of the cross section, a triangle, a hexagon, a semicircle, a bar, a cross, and the shape of the letter L may be cited.

The turning force-transmitting mechanism 505 may be a gear transmission mechanism, a chain transmission mechanism, or a belt transmission mechanism. For example, this transmitting mechanism 505 can be used for reversing the directions of rotation of the knob 921 and the leading end part 3 or varying the speeds of rotation.

Figure 19:
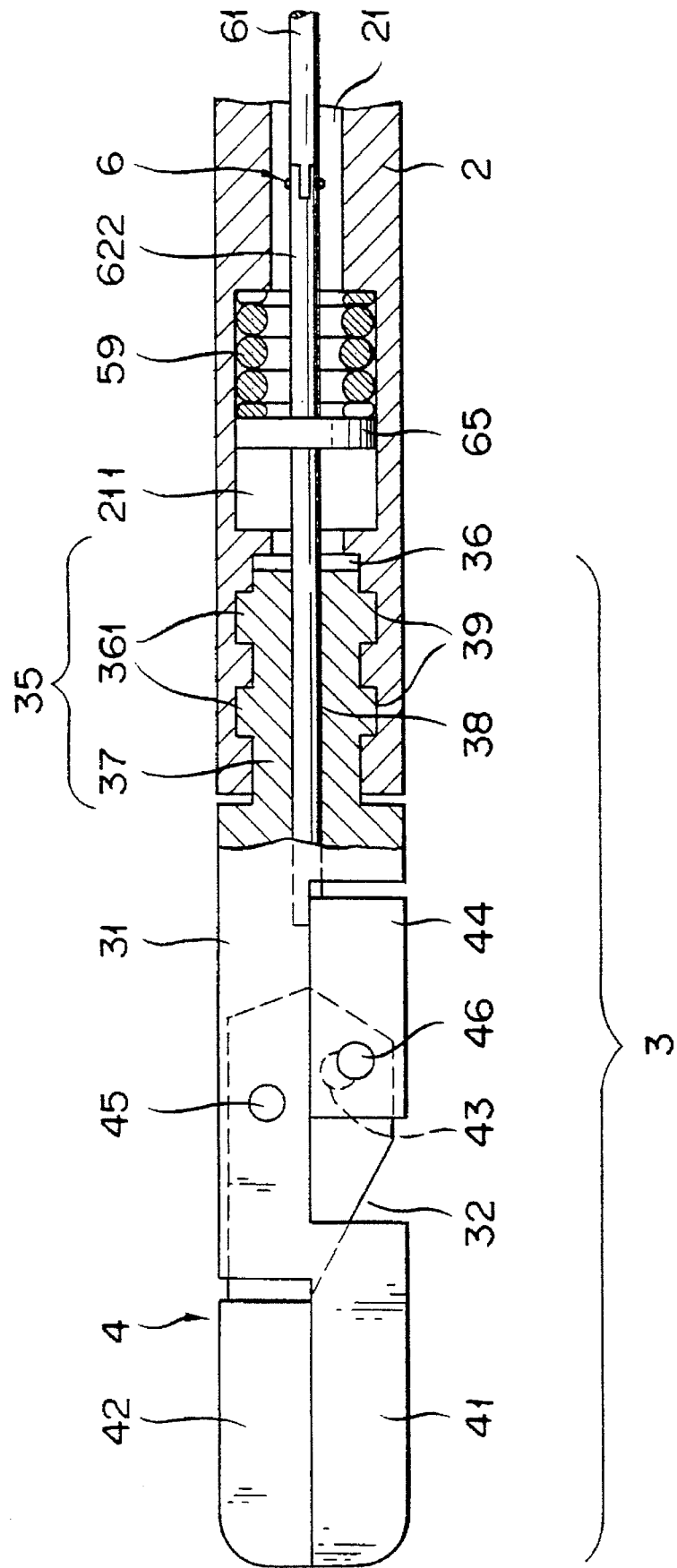
FIG. 19 is a partially sectioned side view illustrating another example of the construction near the leading end part in the modified example mentioned above.

In FIG. 19, the reference numeral 211 stands for a radius-enlarging part and the reference numeral 65 for a flange. The present embodiment is also allowed to form the curving part 23 of the main body 2 of the instrument with the aforementioned plurality of joint rings 24 shown in FIG. 7.

In the surgical instrument 1 of the present embodiment, since the leading end part 3 is rotated relative to the main body 2 of the instrument, the surgically operating means 4 can be rotated without vibration round the axis of the leading end part 3 even when the main body 2 of the instrument is bent or curved halfway along the length thereof. After the surgically operating means 4 has reached a site which is subjected to a surgical treatment, therefore, the posture of the surgically operating means 4 can be suitably varied without affecting the state of access thereof to the site of treatment.

When the manipulation of the surgically operating means 4 and the rotating operation of the leading end part 3 are to be effected concurrently with the transmitting member 6 alone, the transmitting member 6 requires no unduly large space for installation and the main body 2 of the instrument allows further miniaturization.

When the main body 2 of the instrument is adapted to be bent or curved, it permits enlargement of the range in which the surgical treatment can be performed and ensures assumption of a more appropriate posture for the surgical treatment.

While there has been shown and described the surgical instrument of the present invention with reference to illustrated preferred embodiments of the invention, it is to be distinctly understood that the invention is not limited thereto, but may be otherwise variously embodied and practiced without departure from the spirit of the invention. For example, the kind of the surgical instrument of this invention is not limited to the forceps. This invention further embraces scissors, ligators, needleholders, electric scalpels, ultrasonic scalpels, and laser scalpels. As respects the application, the surgical instrument of this invention is not exclusively used for operations under an endoscopic surgery but may be used further for cerebral surgery operations, operations under a thoracoscope, and operations of the urologic organs, for example.

Then, the constructions of the locking means 7, the unlocking means 8, and the manipulating part 9 need not be limited to those shown in the diagrams. The construction of the surgically operating means likewise needs not be limited to that which is rotatable. It may be so constructed as to be opened or closed by a parallel tarnslation, for example. Alternatively, it may be so constructed as to allow revolution of one member like a bobbing forceps, an electric scalpel, or an ultrasonic scalpel. Further, such urging means as the coil springs 59a and 59b may be substituted by springs of other forms such as torsion springs and leaf springs, elastic materials such as rubber, or permanent magnets or electromagnets.

In the surgical instrument of this invention, since the locking means is disposed in or near the leading end part, the posture of the surgically operating means is not affected even when the tension of the transmitting member on the basal end part side past the locking means is varied by a bend or a curve formed in the main body of the instrument or by a change of the environment. In the forceps, for example, the grasping force thereof can be kept constant.

Further, since this surgical instrument does not require the manipulating part to be provided with such locking means as a ratchet mechanism, it allows easy actuation of the surgically operating means and permits simplification of the construction of the manipulating part.

Then, when the main body 2 of the instrument is adapted to be bent or curved, it permits enlargement of the range in which the surgical treatment can be performed and ensures assumption of a more appropriate posture for the surgical treatment.

When the surgical instrument is so constructed as to utilize the rotation of the transmitting member for actuating the surgically operating means, the posture of the surgically operating means is not affected even when the tension of the transmitting member is varied by a bend or a curve formed in the main body of the instrument or by a change of the environment. In the forceps, for example, the grasping force thereof can be kept constant.

We claim:

1. A surgical instrument comprising an elongate main body having a leading end side and a basal end side, said main body including a curving part for enabling at least a portion of the main body to be curved, a leading end part disposed on the leading end side of said main body and provided with surgically operating means for producing operative motion, a manipulating part disposed on the basal end side of said main body and adapted to effect remote control of said surgically operating means, and an elongate transmitting member adapted to transmit operation of said manipulating part to said leading end part, said transmitting member being in the shape of a linear body at least a part of which is flexible, and a locking mechanism located on a leading end side of said curving part for regulating motion imparted by said transmitting member on said leading end part and fixing a posture of said surgically operating means.

2. A surgical instrument according to claim 1, wherein said locking mechanism includes means for allowing said surgically operating means to retain a closed state.

3. A surgical instrument according to claim 1 or claim 2, wherein said locking mechanism is provided with a plurality of balls disposed around said transmitting member and depressing means for pressing said balls against said transmitting member to inhibit longitudinal motion of said transmitting member by virtue of friction generated by the pressure of said balls against said transmitting member.

4. A surgical instrument according to claim 3, wherein said locking mechanism is provided with a ball accommodating part possessed of a tapered inner wall surface having an inside diameter that gradually decreases towards the leading end of the ball accommodating part, said depressing means being composed of a pressing member for pressing said balls against a leading end side of said ball accommodating part and urging means for urging said pressing member toward the leading end thereof.

5. A surgical instrument according to claim 4, which further comprises unlocking means for cancelling a fixed posture of said surgically operating means.

6. A surgical instrument according to claim 5, wherein said unlocking means decreases or eliminates the pressing force exerted by said balls on said transmitting member and allows said transmitting member to move longitudinally.

7. A surgical instrument according to claim 6, wherein said unlocking means is provided with a colliding member adapted to collide against said balls and move said balls towards the basal end side of the pressing member, a wire for drawing said colliding member, and an unlocking operation member for effecting a drawing operation of said wire.

8. A surgical instrument according to claim 1, wherein said transmitting member is provided with conversion means disposed rotatably relative to the main body of said instrument and adapted to convert the rotation of said transmitting member into one of the open-close motion or the rotary motion of said surgically operating means, and said locking means is formed of a supporting part for supporting said transmitting member to effect substantial inhibition of longitudinal motion of the transmitting member.

9. A surgical instrument according to claim 8, wherein said locking mechanism is provided with a rotary shaft connected to a leading end of said transmitting member and a supporting member disposed in said main body of the instrument to support said rotary shaft, said supporting part being provided with a female screw that engages a male screw formed on a periphery of said rotary shaft.

10. A surgical instrument according to claim 8, wherein said locking mechanism is provided with a cam adapted to rotate in consequence of the rotation of said transmitting member, a following member adapted to collide against said cam, and a supporting part disposed in said main body of the instrument to regulate substantial axial motion of said cam and axial motion of said following member.

11. A surgical instrument according to claim 8, wherein said locking mechanism is provided with a worm adapted to rotate in consequence of the rotation of said transmitting member, a worm gear which meshes with said worm, and a supporting part disposed in said main body of the instrument to regulate the substantial axial motion of said worm and the axial motion of said worm gear, and connects said worm gear to said surgically operating means.

12. A surgical instrument according to any one of claims 8 through 11, wherein said locking mechanism is provided with urging means for eliminating backlash or play between said rotary shaft, said cam and worm and said supporting part.

13. A surgical instrument according to claim 1, wherein said surgically operating means is composed of a pair of members at least one of which is adapted to effect open-close motion and is provided with urging means for urging said at least one member in an opening direction.

14. A surgical instrument according to claim 11, wherein said urging means is disposed in or near said leading end part.

15. A surgical instrument according to any one of claims 8, 9, 10, and 11, wherein said manipulating part is provided with a grasping part and a rotatably supported knob and is allowed to connect a rotary shaft of said knob to the basal end part of said transmitting member.

16. A surgical instrument according to claim 8, wherein said manipulating part is provided with a main body, at least one movable handle displaceable relative to said main body, a rotor connected to a basal end part of said transmitting member, and a rotor-driving member for moving relative to the rotor as the movable handle is actuated and rotating the rotor by engaging the rotor, one of said rotor and said rotor-driving member being disposed in said movable handle and the other of said rotor and said rotor-driving member being disposed in said manipulating part.

17. A surgical instrument according to claim 1, including a stationary handle, a movable handle that is displaceable relative to said stationary handle, a rotor disposed in a basal end part of said transmitting member, and a rotor-driving member engaging the rotor and movable relative to the rotor as the movable handle is actuated rotate the rotor.

18. A surgical instrument according to claim 1, wherein said manipulating part is provided with a stationary handle, a movable handle adapted to revolve to vary an opening angle thereof relative to said stationary handle, a rotor-driving member disposed in an end part of said movable handle on a side opposite to a center of rotation of the movable handle or disposed near an end part of said stationary handle on a side opposite to said center of rotation of the movable handle, said rotor-driving member being furnished with a plurality of longitudinally spaced apart receiving areas a rotor connected to a basal end part of said transmitting member, and a plurality of protuberances formed on a periphery of the transmitting member for engagement with said receiving areas.

* * * * *

UNITED STATES PATENT AND TRADEMARK OFFICE
CERTIFICATE OF CORRECTION

PATENT NO. : 5,649,955
DATED : July 22, 1997
INVENTOR(S) : Daijo HASHIMOTO et al It is certified that error appears in the above-identified patent and that said Letters Patent is hereby corrected as shown below:

In Column 14, line 3, delete "Wart" and insert -- part --.

In Column 17, line 28, delete "8a" and insert -- 6a --.

Signed and Sealed this

Thirty-first Day of March, 1998

Attest:

BRUCE LEHMAN

*Attesting Officer*     *Commissioner of Patents and Trademarks*